US006277558B1

(12) United States Patent
Hudson

(10) Patent No.: US 6,277,558 B1
(45) Date of Patent: *Aug. 21, 2001

(54) α-3 CHAIN TYPE IV COLLAGEN POLYNUCLEOTIDES

(75) Inventor: Billy G. Hudson, Lenexa, KS (US)

(73) Assignee: Kansas University Medical Center, Kansas City, KS (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 25 days.

(21) Appl. No.: 09/439,897

(22) Filed: Nov. 12, 1999

Related U.S. Application Data

(60) Continuation-in-part of application No. 09/167,364, filed on Oct. 7, 1998, now Pat. No. 6,007,980, which is a division of application No. 07/621,091, filed on Nov. 30, 1990, now Pat. No. 5,424,408, which is a division of application No. 08/399,889, filed on Mar. 7, 1995, now Pat. No. 5,973,120.

(51) Int. Cl.[7] .............................. C12Q 1/00; G01N 33/53
(52) U.S. Cl. ................................ 435/4; 435/7.1; 530/326; 530/395; 536/23.5
(58) Field of Search ..................... 435/4, 7.1; 530/326, 530/395; 536/23.5

(56) References Cited

U.S. PATENT DOCUMENTS

| 5,424,408 | * | 6/1995 | Reeders et al. ............... 536/23.5 |
| 5,973,120 | * | 10/1999 | Reeders et al. ............... 530/356 |
| 6,007,980 | * | 12/1999 | Reeders et al. ............... 435/4 |

OTHER PUBLICATIONS

Butkowski, R. J. et al. Localization of the Goodpasture epitope to a novel chain of basement membrane collagen. *J. Biol. Chem.* 262, pp. 7874–7877 (1987).

Dehan, P. et al. Sera from patients with anti–GBM nephritis including Goodpasture syndrome show heterogeneous reactivity to recombinant NC1 domain of type IV collagen α chains. *Nephrol. Dial. Transplant.* 11, pp. 2215–2222 (1996).

Fox, J. W. et al. Recombinant nidogen consists of three globular domains and mediates binding of laminin to collagen type IV. *EMBO J.* 10, pp. 3137–3146 (1991).

Geysen, H. M. et al. Use of peptide synthesis to probe viral antigens for epitopes to a resolution of a single amino acid. *Proc. Natl. Acad. Sci.* 81, pp. 3998–4002 (1984).

Gill, S. C. & von Hippel, P. H. Calculation of protein extinction coefficients from amino acid sequence data. *Anal. Biochem.* 182, pp. 319–326 (1989).

(List continued on next page.)

*Primary Examiner*—Louise N. Leary
(74) *Attorney, Agent, or Firm*—McDonnell, Boehnen, Hulbert & Berghoff; David S. Harper

(57) ABSTRACT

An isolated and substantially pure polynucleotide encoding 238 amino acids of the carboxy terminal end of the triple helical domain and all 233 amino acids of the carboxy terminal noncollageneous domain of the bovine α3 chain of type IV collagen. An isolated and substantially pure polynucleotide encoding 218 amino acids of the carboxy terminal noncollagenous domain of the human α3 chain of type IV collagen. Such polynucleotides are useful to express large amounts of proteins in vectors and such expressed proteins are useful to detect Goodpasture antibodies in blood and to remove Goodpasture antibodies from the bloodstream of patients suffering from Goodpasture syndrome.

7 Claims, 18 Drawing Sheets

OTHER PUBLICATIONS

Figure 3:
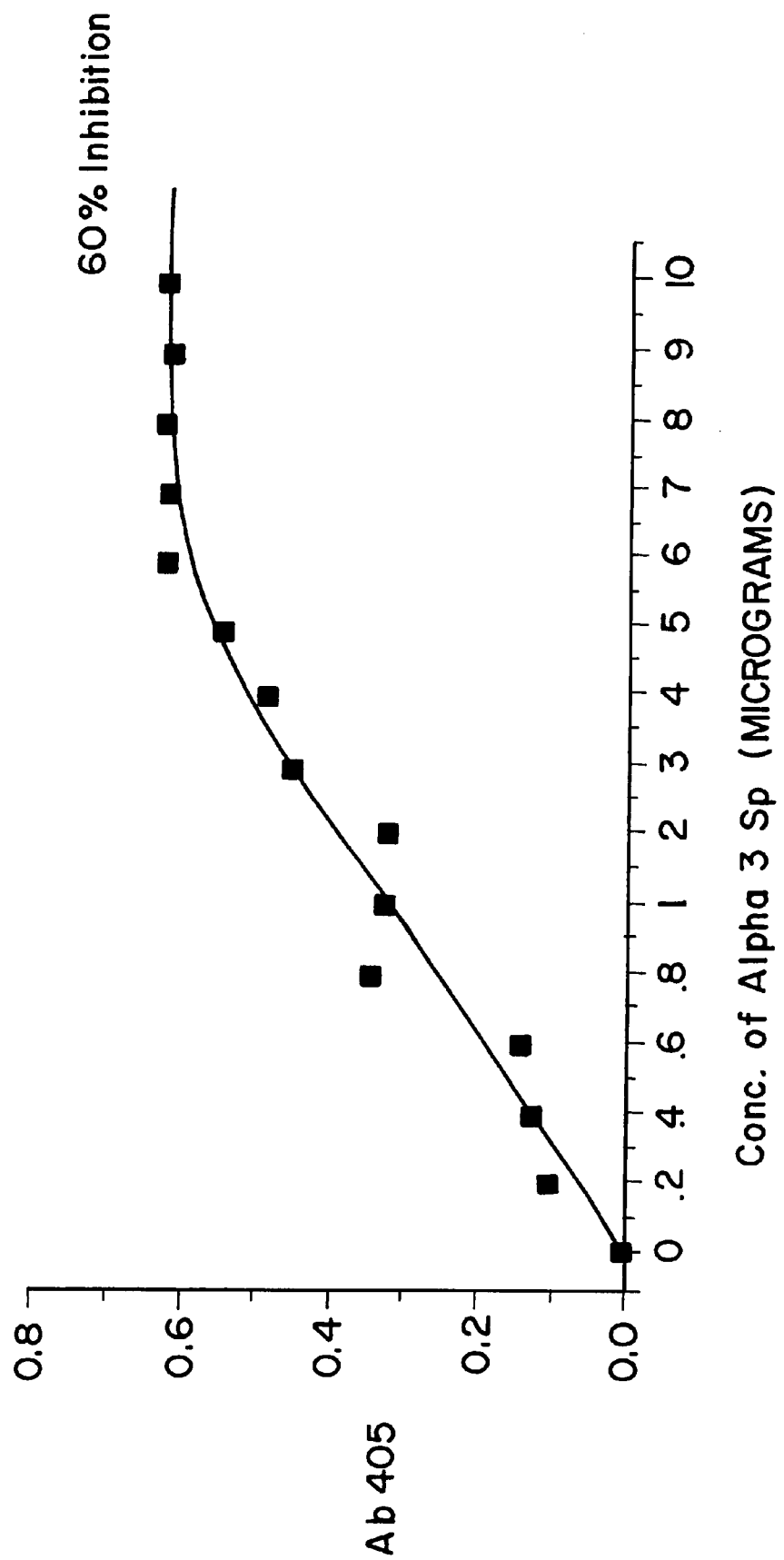

Gunwar, S. et al. Glomerular basement membranes: Identification of a novel disulfide–cross-linked network of α3, α4, and α5 chains of type IV collagen and its implications for the pathogenesis of Alport syndrome. *J. Biol. Chem.* 273, pp. 8767–8775 (1998).

Gunwar, S. et al. Glomerular basement membranes: Identification of dimeric subunits of the noncollagenous domain (hexamer) of collagen IV and the Goodpasture antigen. *J. Biol. Chem.* 266, pp. 15318–15324 (1991).

Hellmark, T. et al. Epitope mapping of anti–glomerular basement membrane (GBM) antibodies with synthetic peptides. *Clin. Exp. Immunol.* 105, pp. 504–510 (1996).

Hellmark, T. et al. Characterization of anti–GBM antibodies involved in Goodpasture's syndrome. *Kidney Int.* 46, pp. 823–829 (1994).

Henriksson, E. W. & Pettersson, I. Autoepitope–mapping of the U1–70K protein with human–Drosophila chimeric proteins. *J. Autoimmun.* 10, pp. 559–568 (1997).

Hsia, R.–C. et al. Use of chimeric recombinant polypeptides to analyse conformational, surface epitopes on trypanosome variant surface glycoproteins. *Mol. Microbiol.* 19, pp. 53–63 (1996).

Hudson, B. G. et al. Type IV collagen: Structure, gene organization, and role in human diseases. Molecular analysis of Goodpasture and Alport Sydromes and diffuse Leiomyomatosis. *J. Biol. Chem.* 268, pp. 26033–26036 (1993).

Jones, S. & Thornton, J. M. Principles of protein–protein interactions. *Proc. Natl. Acad. Sci.* 93, pp. 13–20 (1996).

Kalluri, R. et al. The Goodpasture autoantigen: Structural delineation of two immunologically privileged epitopes on α3(IV) chain of type IV collagen. *J. Biol. Chem.* 271, pp. 9062–9068 (1996).

Kalluri, R. et al. Identification of the α3 chain of type IV collagen as the common autoantigen in antibasement membrane disease and Goodpasture syndrome. *J. Am. Soc. Nephrol.* 6, pp. 1178–1185 (1995).

Kalluri, R. et al. Goodpasture syndrome: Localization of the epitope for the autoantibodies to the carboxyl–terminal region of the α3(IV) chain of basement membrane collagen. *J. Biol. Chem.* 266, pp. 24018–24024 (1991).

Kefalides, N. A. et al. Identification of antigenic epitopes in type IV collagen by use of synthetic peptides. *Kidney Int.* 43, pp. 94–100 (1993).

Laemmli, U. K. Cleavage of structural proteins during the assembly of the head of bacteriophage T4. *Nature* 227, pp. 680–685 (1970).

Laver, W. G. et. al. Epitopes on protein antigens: Misconceptions and realities. *Cell* 61, pp. 553–556 (1990).

Levy, J. B. et al. Mapping B cell epitopes in Goodpasture's disease. *J. Am. Soc. Nephrol.* 8, pp. 1698–1705 (1997).

Levy, J. B. et al. Epitope analysis of the Goodpasture antigen using a resonant mirror biosensor. *Clin. Exp. Immunol.* 106, pp. 79–85 (1996).

Mariyama, M. et al. Complete primary structure of the human α3(IV) collagen chain: Coexpression of the α3(IV) and α4(IV) collagen chains in human tissues. *J. Biol. Chem.* 269, pp. 23013–23017 (1994).

Mayer, U. et al. Recombinant expression and properties of the Kunitz–type protease–inhibitor module from human type VI collagen α3(VI) chain. *Eur. J. Biochem.* 225, pp. 573–580 (1994).

Meyers, K. E. et al. Human Goodpasture anti–α3(IV)NC1 autoantibodies share structural determinants. *Kidney Int.* 53, pp. 402–407 (1998).

Neilson, E. G. et al. Specificity of Goodpasture autoantibodies for the recombinant noncollagenous domains of human type IV collagen. *J. Biol. Chem.* 268, pp. 8402–8405 (1993).

Netzer, K.–O. et al. Comparative analysis of the noncollagenous NC1 domain of type IV collagen: Identification of structural features important for assembly, function, and pathogenesis. *Protein Sci.* 7, pp. 1340–1351 (1998).

Penades, J. R. et al. Characterization and expression of multiple alternatively spliced transcripts of the Goodpasture antigen gene region. *Eur. J. Biochem.* 229, pp. 754–760 (1995).

Pusey, C. D. et al. A single autoantigen in Goodpasture's syndrome identified by a monoclonal antibody to human glomerular basement membrane. *Lab. Invest.* 56, pp. 23–31 (1987).

Ryan, J. J. et al. Recombinant α–chains of type IV collagen demonstrate that the amino terminal of the Goodpasture autoantigen is crucial for antibody recognition. *Clin. Exp. Immunol.* 113, pp. 17–27 (1998).

Sado, Y. et al. Induction of anti–GBM nephritis in rats by recombinant α3(IV)NC1 and α4(IV)NC1 of type IV collagen. *Kidney Int.* 53, pp. 664–671 (1998).

Schwab, C. et al. Mapping antibody binding sites on cytochrome c with synthetic peptides: Are results representative of the antigenic structure of proteins? *Protein Sci.* 2, pp. 175–182 (1993).

Saus, J. et al. Identification of the Goodpasture antigen as the α3(IV) chain of collagen IV. *J. Biol. Chem.* 263, pp. 13374–13380 (1988).

Tzartos, S. J. et al. The main immunogenic region (MIR) of the nicotinic acetylcholine receptor and the anti–MIR antibodies. *Mol. Neurobiol.* 5, pp. 1–29 (1991).

Wieslander, J. et al. Characterization of the human Goodpasture antigen. *Clin. Exp. Immunol.* 69, pp. 332–340 (1987).

Wieslander, J. et al. Isolation of the specific glomerular basement membrane antigen involved in Goodpasture syndrome. *Proc. Natl. Acad. Sci. USA* 81, pp. 1544–1548 (1984).

Yurchenco, P. D. et al. The α chain of laminin–1 is independently secreted and drives secretion of its β– and γ–chain partner. *Proc. Natl. Acad. Sci. USA* 94, pp. 10189–10194 (1997).

\* cited by examiner

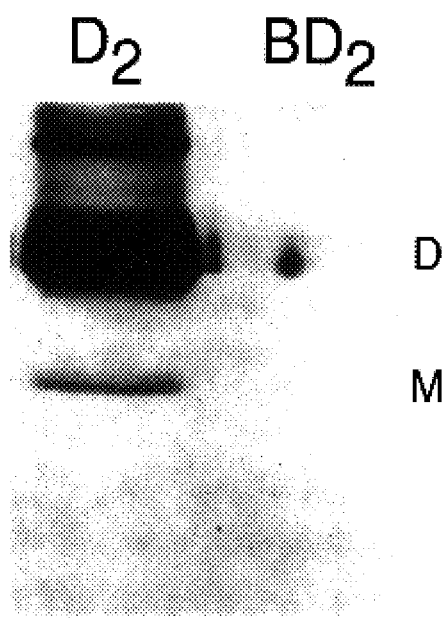
FIG.1
FIG.2

| | | |
|---|---|---|
| F1: | 5' - AAGCCNGGNGA(C,T)ACAGG -3' | (5) |
| F2: | 5' - AAGCCNGGNGA(C,T)ACCGG -3' | (5) |
| F3: | 5' - AAGCCNGGNGA(C,T)ACGGG -3' | (5) |
| F4: | 5' - AAGCCNGGNGA(C,T)ACTGG -3' | (5) |
| R1: | 5' - TA(A,G)TG(T,C)CTNGT(A,G)AANACAAA -3' | (28) |
| R2: | 5' - TA(A,G)TG(T,C)CTNGT(A,G)AANACGAA -3' | (28) |
| R3: | 5' - TA(A,G)TGNCGNGT(A,G)AANACAAA -3' | (28) |
| R4: | 5' - TA(A,G)TGNCGNGT(A,G)AANACGAA -3' | (28) |
| | | |
| FA: | 5' - GCNGGNCGNGTNATGCG -3' | (14) |
| FB: | 5' - GCNGGNCGNGTNATGAG -3' | (14) |
| FC: | 5' - GTNTT(C,T)ACNAG(A,G)CA(C,T)TATC -3' | (22) |
| FD: | 5' - CCAGG(A,C)GA(C,T)AC(A,C,T)GGNCC(A,C,T)CCAG -3' | (6) |
| RA: | 5' - CAGGAAGGGCAT(G,T)GTGCTGAA -3' | [165] |
| RB: | 5' - GG(G,C)GCCTCACACACAG(A,C)ACA -3' | [317] |
| RC: | 5' - TTGCAG(A,T)ACAGGAAGGGCAT -3' | [173] |
| RD: | 5' - TTGCAG(A,T)ACAGGAAGGG -3' | [173] |
| | | |
| F9*: | 5' - CCCGATGGGTTGCCAGGATCCAT -3' | [-42] |
| R9*: | 5' - TGACTATGCCTGGTCACAAG -3' | [37] |

FIG. 7

Figure 11. The PCR primers sequences and the restriction enzymes used for cloning of the recombinant proteins.

| Product | | Primer sequences (5'→3') | Enzyme |
|---|---|---|---|
| Vector intermediate | A1[a] | CAAGCTAGCGCGCCGCTCGAGATGCATCTAGAGGGCCC | NheI |
| | B1[a] | GCCGCTAGCTTGTCATCGTCGTCCTTGTAGTCGGCTAGTGGGCTGCCAGAGCCCT[b] | NheI |
| pRc-X | A2 | AGCTCTAGAGTCATCGATGTTAACCGCGGCCCTATTCTATAGTGTC | XbaI |
| | B2 | CCCTCTAGATGCATCTCGAGCGGC | XbaI |
| α1(IV)NC1 | A3 | GCTAGCATCTGTTGATCACGGCTTCC | NheI |
| | B3 | CCGCGGTAGCTGAGTCAGGCTTCATTATG | SacII |
| C2 | A4 | AGTGGAAGACGGGACAGTGCCACTCTACAGTGGTACTCTTTGCTCTACGTG | BbsI |
| | B4 | TGCAGAAGACCTGTCCCCTCTGGACATGAAGGAATTGCTGTTGTTGACTATGCCTGGTCACAAGG | BbsI |
| C3 | A5 | GAGCGAAGACAAGAATGTCAGAAAGCCTATTCCGTCCACCTTGAAGGCAG | BbsI |
| | B5 | GGCTGAAGACACACATTCTTTCTGGGTTTAATGAGGCGAGCCAAAAGCTGTAAGC | BbsI |
| C5 | A6 | CAGTGAAGACTCCCATTACTGGCAGAGCCCTTGAGCCATTTATTAGTAGGTGTGCTG | BbsI |
| | B6 | ACGTGAAGACTAATGGGAGCCATGTTCATTGCCATCAGCTCAGGGGTGGACAGCCAGTAC | BbsI |
| C6 | A7 | CAGCGAAGACTGTCCTCACGGCTGGATTTCTCTGGAAAGGCTACTCTTTTGTGATGCAC | BbsI |
| | B7 | AGATGAAGACTGAGGACATGTCAGTGCTGGCTGTGCTGTGCACGGCCATC | BbsI |
| C1 | A8 | AATGCTAGCAACCTGGACAACGAGACGAGGCTTCCTTGTGACCAGG | NheI |
| | B8 | GACATCGATCGAGTCAGGCTTCATTATG | ClaI |
| C4 | A9 | ACGTGAAGACTCAGGTGTGCATGAAGAAAAGACACTAATGAAGCCTGACTCAGCTAGG | BbsI |
| | B9 | CTTCGAAGACACACCTGACAGCGACTTATTATTTTTCCAGCTCCCCTGCCTTCAAG | BbsI |
| C7 | A10 | ATATGCTAGCTGGTTTGAAAGGAAAACGTGGAGACAGTGGATCACCTGCAACCTGGACAACGAGA | NheI |
| | B10 | GACATCGATCGAGTCAGGCTTCATTATG | ClaI |
| α1(IV)NC1 +Gly-X-Y | A11 | ATATGCTAGCAGGGCCTCCAGGCACCCATCTGTTGATCACGGCTTC | NheI |
| | B11 | GACATCGATCGAGTCAGGCTTCATTATG | ClaI |
| C8 | A12 | GATCGAAGACCACCGTGAAGGCAGGGAGCTGGAA | BbsI |
| | B12 | CAGTGAAGACTCACGGTGGACGGAATAGGCTTTC | BbsI |

[a] A, forward primer; B, reverse primer.
[b] FLAG sequence underlined.

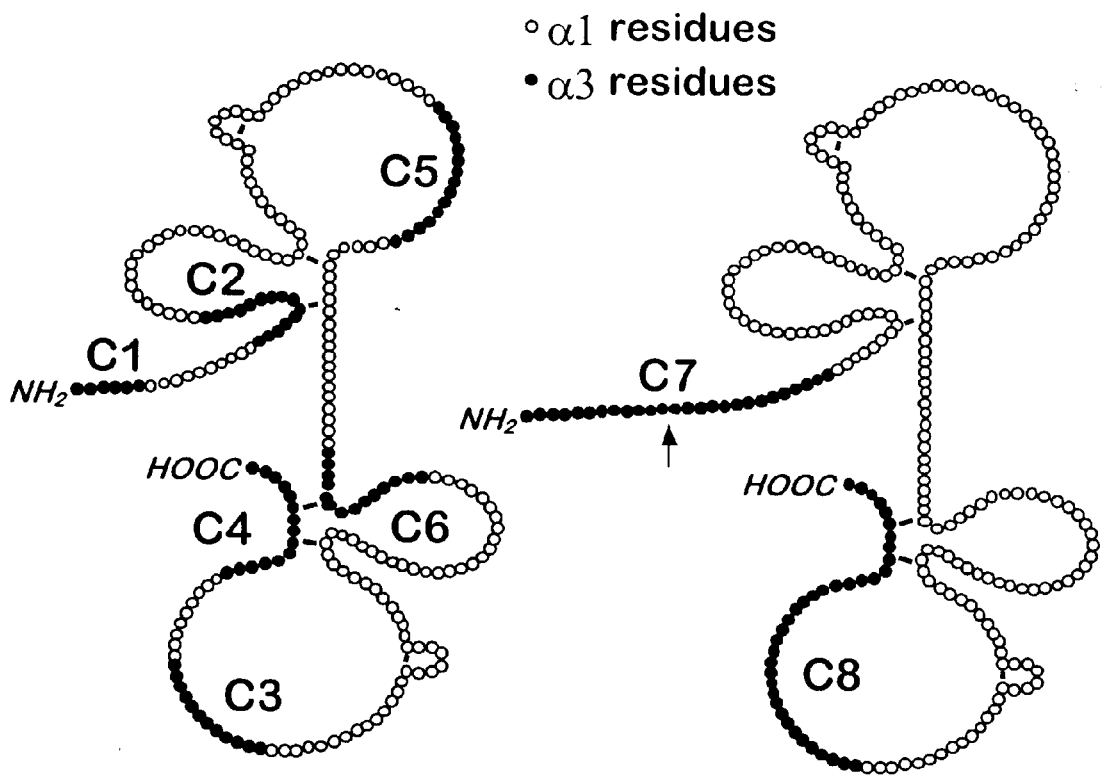

○ α1 residues
● α3 residues

C1  α1 ..SVDH
    α3 ATWTTR

C2  α1 IDDPQCPSGTKILYH
    α3 TAIPSCPEGTVPLYS

C3  α1 TIERSEMFKKPT
    α3 SLNPERMFRKPI

C4  α1 RTHVSRCQVCMRRT.
    α3 EKIISRCQVCMKKRH

C5  α1 PMPMSMAPITGENIR
    α3 LMPMNMAPITGRALE

C6  α1 IQIPPCPSGWSSLWI
    α3 TDIPPCPHGWISLWK

C7  α1 GLPGSMGPPGTP..SVDHGFLVTRHS
    α3 GLKGKRGDSGSPATWTTRGFVFTRHS

C8  α1 TIERSEMFKKPTPSTLKAGELRTHVSRCQVCMRRT.
    α3 SLNPERMFRKPIPSTVKAGELEKIISRCQVCMKKRH

Figure 12

Figure 17. Relative immunoreactivity against various α3(IV)NC1 regions in eight GP sera.

| Serum | Specificity[a] | | | α1 cross-reactivity | Not assigned[c] |
|---|---|---|---|---|---|
| | $E_A$[b] | $E_B$[b] | $E_{AB}$[b] | | |
| GP-1 | 41% | 5% | 63% | 3% | 34% |
| GP-2 | 47% | 6% | 53% | 15% | 31% |
| GP-3 | 31% | 21% | 52% | 11% | 37% |
| GP-4 | 51% | 8% | 80% | 3% | 18% |
| GP-5 | 64% | 11% | 84% | 8% | 9% |
| GP-6 | 58% | 33% | 88% | 5% | 6% |
| GP-7 | 26% | 56% | 70% | 15% | 15% |
| GP-8 | 56% | 3% | 56% | 6% | 38% |

[a] The inhibition of Goodpasture sera binding to a plate coated with α3(IV)NC1 was measured in the presence of soluble C2, C6, C2·6 chimeras and α1(IV)NC1 at 10 µg/ml (Fig. 6B). The inhibition produced by α1(IV)NC1 was subtracted from the values obtained with the chimeric proteins to account for the contribution of cross-reactivity, then the results were normalized to the inhibition obtained with the control α3(IV)NC1 domain (100%).

[b] $E_A$, $E_B$, and $E_{AB}$ represent the α3(IV)NC1 sequences present in C2, C6 and C2·6 chimeras, respectively, i.e. residues 17-31, 127-141, and both sequences.

[c] The specificity not assigned represented the amount of binding that could be inhibited by α3(IV)NC1, but not by C2·6 chimera.

# α-3 CHAIN TYPE IV COLLAGEN POLYNUCLEOTIDES

This application is a CIP of Ser. No. 09/167,364 filed Oct. 7, 1998 now U.S. Pat. No. 6,007,980 which is a division of Ser. No. 07/621,091 filed Nov. 30, 1990 now U.S. Pat. No. 5,424,408 which is a division of 08/399,889 filed Mar. 7, 1995 now U.S. Pat. No. 5,973,120.

GOVERNMENT RIGHTS

This invention was made with United States government support under Grant DK40703 from the National Institute of Health. The United States government has certain rights in this invention.

BACKGROUND OF THE INVENTION

1. Field of the Invention

The present invention concerns alpha-3 chain type IV bovine and human polynucleotides and peptides expressed by such polynucleotides which are useful in detecting Goodpasture antibodies and treating Goodpasture syndrome.

2. Background Information

The major structural component of mammalian basement membranes, type IV collagen, is composed of a number of distinct polypeptide chains (Timpl et al. 1981; Martin et at 1988; Timpl 1989). The most abundant species, α1(IV) and α2(IV) have been extensively characterized in man and mouse and an α type chain from Drosophila also been identified (Soinmen et al. 1987; Blumberg et al. 1988; Hostikka and Tryggvason 1988; Savs et al. 1989; Muthukumaran et al. 1989). Characteristics of these collagens include a highly conserved carboxy-terminal noncollagenous (NC1) domain of ~229 residues, a shorter amino-terminal globular domain (7S domain) and a triple helical collagenous domain, in which interruptions occur in the Gly-Xaa-Xaa-Yaa repeat motif, giving a degree of flexibility to the triple helix. Within the membrane matrix the individual collagen chains exist as heterotrimer, which form a supra-molecular structure via interactions between the 7S domains of 4 molecules and the NCI domains of 2 heterotrimers (Timpl et al 1981).

Bacterial collagenase digestion releases the NCI domains from the other components of basement membrane as hexamers, comprised of the 3 NC1 domains from each of 2 interacting colllagen heterotrimers. The NCI domains can be further separated on the basis of molecular weight by denaturing polyacrylamide gel electrophoresis. This results in a number of separate monomeric and dimeric subunits (Mr=24,500–28,300 and 40,000–50,70000 respectively), including several which are distinct from the α1(IV) and α2(IV) chains (Butkowski et al. 1985; Wieslander et al. 1985). The monomeric subunits that result from collagenase digestion of human glomerular basement membrane (GBM) have been termed M24, M26, M28+++ and M28+, while the equivalent subunits of bovine basement membranes have been termed M1a, M1b, M2* and M3 (Kleppel et al. 1986; Butkowski et al. 1987). M24 (or M1a) and M26 (or M1b) are the NC1 domains of the α1(IV) and α2(IV) chains. M28+++ (or M2*) and M28+ (or M3) are the NC1 domains of 2 novel collagen chains termed α3(V) and α4(V). Short segments of the junction between the collagenous and NCI domains of human and bovine α3(IV) and α4(IV) peptides have been sequenced, confirming that they have a type IV collagen structure (Saus et al 1988; Butkowski et al. 1990).

The α3(IV) chain and the α4(IV) chain are of particular interest as such chains have been implicated in the pathogenesis of Goodpasture syndrome and Alport-type familial nephritis, clinical syndromes that affect GBM and cause functional kidney impairment (Hudson et al. 1989). Goodpasture syndrome is an autoimmune disorder characterized by glomerulonephritis, lung hemorrhage and anti-GBM antibody formation (Glassock et al. 1986). The nephritis and lung damage are mediated by these anti-GBM antibodies which are primarily targeted at the NC1 domain (M28+++) of α3(IV) (Butkowski et at 1985; Wieslander et al. 1985; Kleppel al.1986). Alport syndrome is an inheritable disorder characterized by glomerulonephritis, sensorineural hearing loss and various abnormalities of the lens of the eye (Grunfeld, 1985). Ultrastructural GBM abnormalities frequently observed in the syndrome including thinning, diffuse splitting and multilamination of the lamina dense (Hinglais et al. 1972; Yoshikawa et al. 1981). Several investigators have reported that the GBM of some individuals with Alport syndrome does not react in vitro with Goodpasture antibodies nor with a monoclonal antibody that recognizes a Goodpasture epitope, suggesting that there is an abnormality of the α3(IV) chain in these patients (Olsen et al 1980; Jervis et al. 1981; Jeraj et al. 1983; Kashtan et al. 1986; Savage et at 1986; Kleppel et al. 1987).

Recently a gene encoding another novel human type IV collagen chain, COL4A5, was cloned, on the basis of homology with the α1(IV) and α2(IV) chains (Hostikka et al. 1990; Myers et al. 1990. The existence of such a chain had not been expected from biochemical or immunological studies of GBM (glomerular basement molecular), and yet antibodies raised to a peptide fragment synthesized from the predicted amino acid sequence of α5(IV) localized this chain to the GBM (Hostikka et at 1990). COL4A5 maps to Xq22, a region known from genetic linkage studies to contain a locus for Alport Syndrome (Atkin et al. 1988; Brunner et al. 1988; Flinter al. 1988). Further, COL4A5 has been shown to be musted in 3 of 18 large kindreds with the disease (Barker et al. 1990).

SUMMARY OF THE INVENTION

The present invention concerns an isolated and substantially pure polynucleotide enhancing 238 consecutive amino acids from the carboxy terminal end of the triple helical domain and all 233 amino acids of the carboxy terminal noncollageneous domain of the bovine α3 chain of type IV collagen and a nucleotide sequence of said polynucleotide. The invention is also directed to a deduced amino acid sequence of the bovine α3 chain of type IV collagen.

The present invention also relates to an isolated and substantially pure polynucleotide encoding 218 consecutive amino acids of the carboxy terminal noncollagenous domain of the human α3 chain of type IV collagen and a nucleotide sequence of said polynucleotide. The invention is also directed to a deduced amino acid sequence of the human α3 chain of the type IV collagen.

The above described polynucleotides can be used to express large amounts of proteins in vectors. Such proteins can be used to detect Goodpasture antibodies from the bloodstream of patients suffering from Goodpasture syndrome.

The present invention also concerns a peptide having no more than 218 amino acids of the human α3 chain of type IV collagen comprising the following amino acid sequence:

ISRCQVCMKKRH (Iso Ser Arg Cys Gln Val Cys Met Lys Lys Arg His).

The invention also relates to 6 to all 12 consecutive amino acids of the sequence ISRCQVCMKKRH.

The invention also relates to a method for detecting Goodpasture antibodies from a bodily fluid or tissue from a patient, for example, a human, comprising contacting a bodily fluid or tissue from the patient, for example, a human, for example, contacting blood or a liquid fraction thereof, e.g. serum or plasma, with a peptide having no more than 218 amino acids of the human α3 chain of type IV collagen comprising the following amino acid sequence: ISRCQVCMKKRH, whereby if Goodpasture antibodies are present a product will form of the antibodies and peptide and detecting for the presence of Goodpasture antibodies by, for example, by labelling the peptide, e.g., using an ELISA technique, i.e., using an enzyme label and detecting for the presence of the label on the antibody-peptide product.

The present invention is further directed to a therapeutic method of treating Goodpasture syndrome in a patient by neutralizing Goodpasture antibodies in the whole blood or liquid fraction thereof, e.g., plasma or serum, of the patient, for example, a human patient, by contacting the whole blood or liquid fraction thereof from the patient with an effective antibody neutralizing amount of a peptide having no more than 218 amino acids of the human α3 chain of type IV collagen comprising the following amino acid sequence: ISRCQVCMKKRH. In such therapeutic method, the peptide is preferably bound to a solid support and the blood, serum or plasma from the patient passes over the peptide bound to the solid support, whereby the peptide captures the Goodpasture antibodies to remove such antibodies from the patient's blood, serum or plasma. The blood, serum or plasma with some, all or most of the Goodpasture antibodies removed is then returned to the bloodstream of the patient intravenously.

BRIEF DESCRIPTION OF THE DRAWINGS

FIG. 1 is a Western blot of dimer fraction D2 and NC1 hexamer before and after biotinylation samples. After biotinylatioin, reactivity of dimer fraction D2 with GP-antibodies is lost. Biotinylation of the native NC1 domain does not affect its reactivity with GP-antibodies indicating that the GP-epitope is sequestered inside the hexamer as previously found.

FIG. 2 is a Western Blot of the Control D1 (lane 1) and Carboxypeptidase Y treated D2 (lane 2), using GP sera.

FIG. 3 is a graph depicting the results of an inhibition Elisa. The plates were coated with 400 ngs of α3NC1 monomer (Goodpasture antigen) and subsequently blocked with 1% BSA. The primary antibody was preincubated with peptide for 12 hours and then the reaction mixture was treated with the Goodpasture antigen. Secondary antibodies were against human IgG and HRP conjugated. The assay was measured at Ab 405.

FIG. 4 is a graph depicting the results of an inhibition ELISA. The same conditions as in FIG. 3 were used, except in this case the peptide was allowed to compete with the Goodpasture (GP) antigen for GP antibodies for 12 hours.

FIG. 5 is a graph which depicts the results of a direct ELISA. The plates were coated with 20 micrograms of peptide and analyzed for its reactivity with the GP antibodies. The other conditions are same as FIG. 3.

FIG. 6 is a Western blot analysis of the reactivity of Goodpasture antigen (α3NC1 Monomer) with the peptide bound GP antibodies from a cynogen bromide activated Sepharose 4B column. 1 mg of α3 peptide was coupled to the matrix for 12 hours upon packing it on a column, GP sera (1:10 dilution) was repeatedly passed through the column for 5 times and the non-specifically bound antibodies removed, upon which the bound antibodies were eluted at low pH and immediately neutralized and dialysed against 1× PRS pH 7.4. This sample was then used for a Western blot analysis.

FIG. 7 depicts oligonucleotide primer sequences. N is A or C or G or T. Numbers in parentheses ( ) at the right indicate the number of the α3(IV) amino acid from which the 5' end of the nucleotide sequence was derived. The α3(IV) amino acid sequence is from reference 13, numbering the first glycine residue of M2* as 1. Numbers in parentheses [ ] at the right indicate the number of the α1(IV) nucleotide from which the 5' end of the nucleotide sequence was derived. The α1(IV) sequence is from reference 29.

FIG. 8*a* depict blots concerning PCR reaction products obtained using a bovine genomic template. The primers used are indicated below each lane. F9* and R9* are primers complementary to corresponding regions of human α1(IV). Arrows mark the positions of the 1018 and 516/506 bp marker fragments (lane M) and the expected position of a 68 bp fragment. PCR conditions: denature 94° C.;1 min: anneal 60° C.;15 secs: extend 72° C.;30 secs (30 cycles).

FIG. 8*b* depicts blots concerning reactions identical to those in FIG. 8*a* except for the PCR cycling profile: denature 94° C.;1 min. anneal 68° C.;30 secs (2 cycles): denature 94° C.;1 min, anneal 66° C.;30 secs (2 cycles: denature 94° C.;1 min, anneal 64° C.;30 secs (2 cycles): denature 94° C.;1 min, anneal 58° C. for 28 cycles.

FIG. 9 is a restriction map and sequencing strategy for KEMC15. cDNA from KEMC15 is represented by the solid thick line. pBluescript by the open-ended hollow bars and λgt11 by the solid thin line. Solid arrows indicate the length and orientation of sequence analysis. Open arrows (→) show the position of the λgt11 primers used to amplify the cDNA library insert. The position of the probe KEM68 is shown by a hatched box. Restriction sites for BamHl (B), EcoRl (E), EcoRv(V), Pstl,(P), Pvull(Pv), Rsal(R), Smal(S) and Tagl(T) are indicated.

FIG. 10. Expression of recombinant NC1 domains and chimeric constructs.

Bottom: Schematic of pRc/CMV. Key elements of the vector are shown. Middle: Expression cassette and multiple cloning sites inserted between CMV promoter ($P_{CMV}$) and bovine growth hormone poly adenylation signal (BGH, pA). The position of the translation start codon (ATG) is indicated. Top: Schematic representation of the α1(IV)NC1 insert cloned between Nhel and SacII sites. The position of the stop codon is shown at the right (TAA). The principle of inverse PCR for the insertion of α3(IV)NC1 sequences is illustrated in the dashed circle (see Methods).

FIG. 11. PCR primer sequences and the restriction enzymes used for cloning of the recombinant proteins.

FIG. 12. Schematic illustration of the α1/α3(IV)NC1 chimeric constructs.

At the positions indicated by filled circles, sequences of amino acids from α3(IV)NC1 replaced those in the α1(IV) NC1 (open circles). The disulfide bonds are represented as short lines closing the loops. The arrow indicates the junction between the collagenous and NC1 domains.

FIG. 13. Western blot analysis of the α1/α3(IV) chimeras with GP sera.

SDS-PAGE was performed in 4–20% gradient gels under non-reducing conditions and the proteins were stained with Coomassie Blue (a). The molecular weight markers (MW std) indicated by arrows were 60 40, 3, 20 and 15 kDa. Western blotting was performed using GP-1 (b), GP-2 (c) and GP-6 (d) sera at 1:100 dilution.

Figure 14:
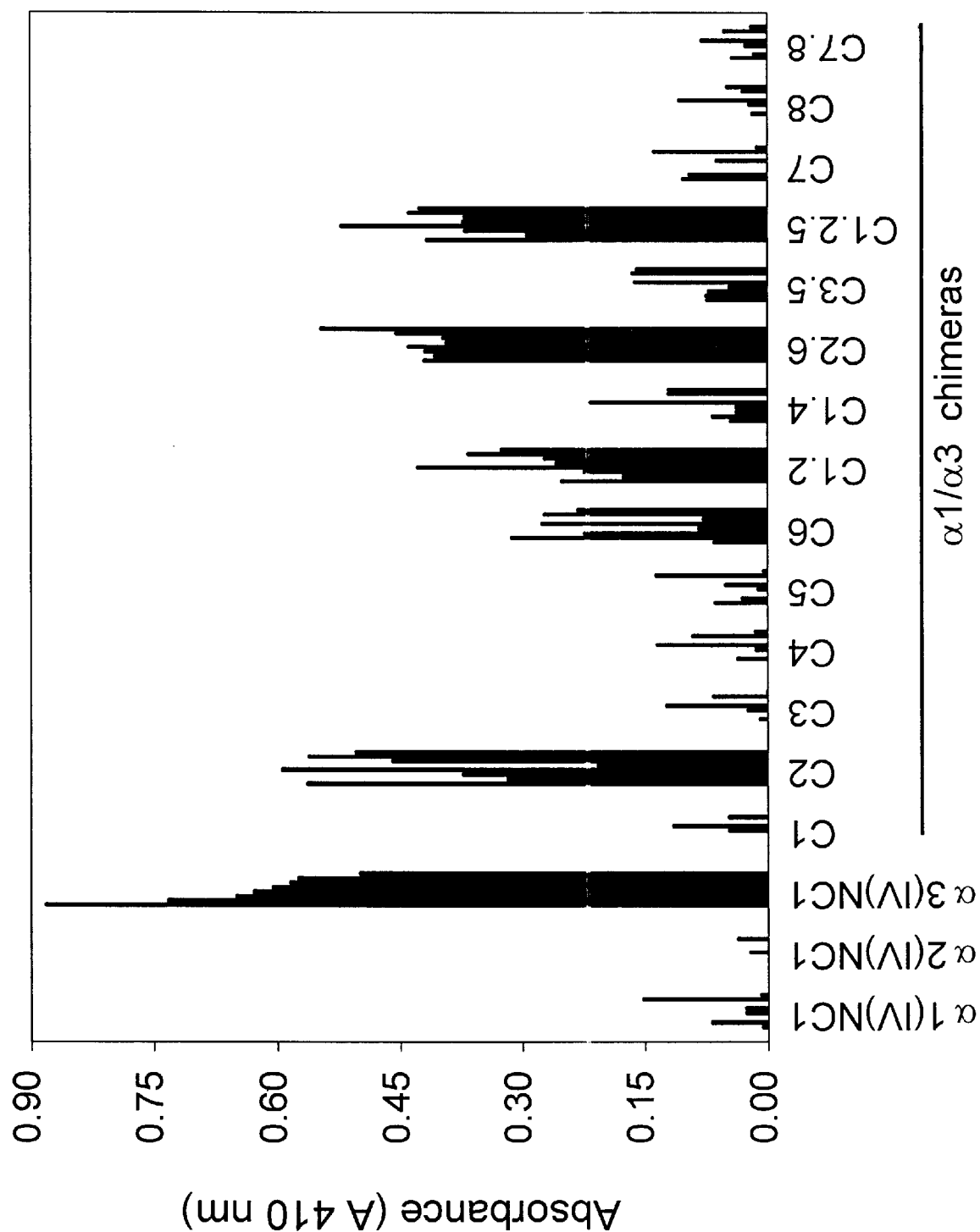

FIG. 14. Direct ELISA of fourteen α1/α3(IV) chimeras with GP sera.

Proteins were coated onto plastic plates at 100 ng/well. Recombinant α1-, α2- and α3(IV)NC1 domains were used as controls. Eight GP sera were diluted in the incubation buffer proportionally to their titers (1:1000 for the reference serum GP-1). Two normal sera were used as negative controls at 1:50 dilution. The average ELISA reading of the normal sera (0.09±0.04 $A_{410}$) was subtracted from the values obtained with GP sera.

Figure 15:
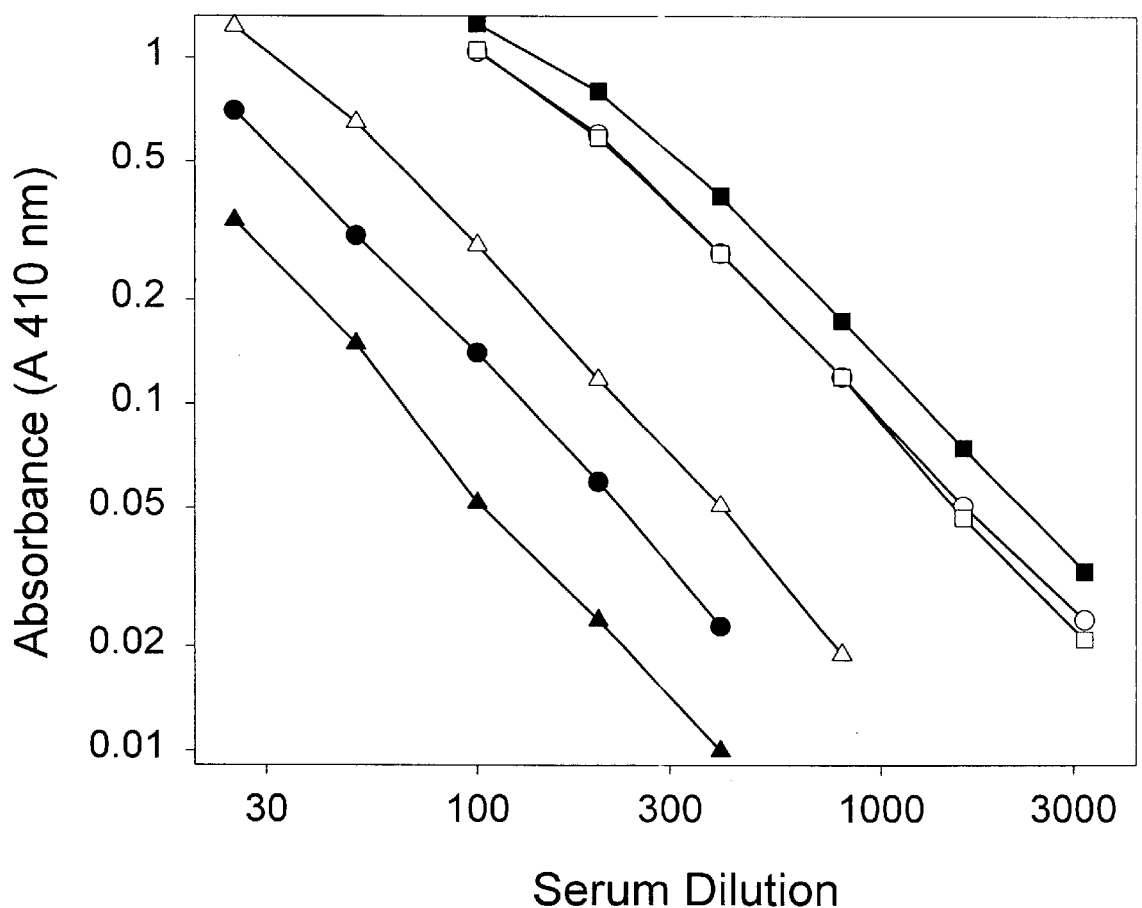

FIG. 15. Titration of GP-1 serum binding to α1/α3(IV) chimeras.

The wells were coated with 100 ng antigen: C2 (open circles), C6 (open triangles) and C2•6 (open squares) chimeras, and controls α1(IV) (filled circles), α2(IV) (filled triangles) and α3(IV) (filled squares) NC1 domains. The binding to immobilized proteins of serial dilutions of the serum was measured by direct ELISA.

Figure 16:
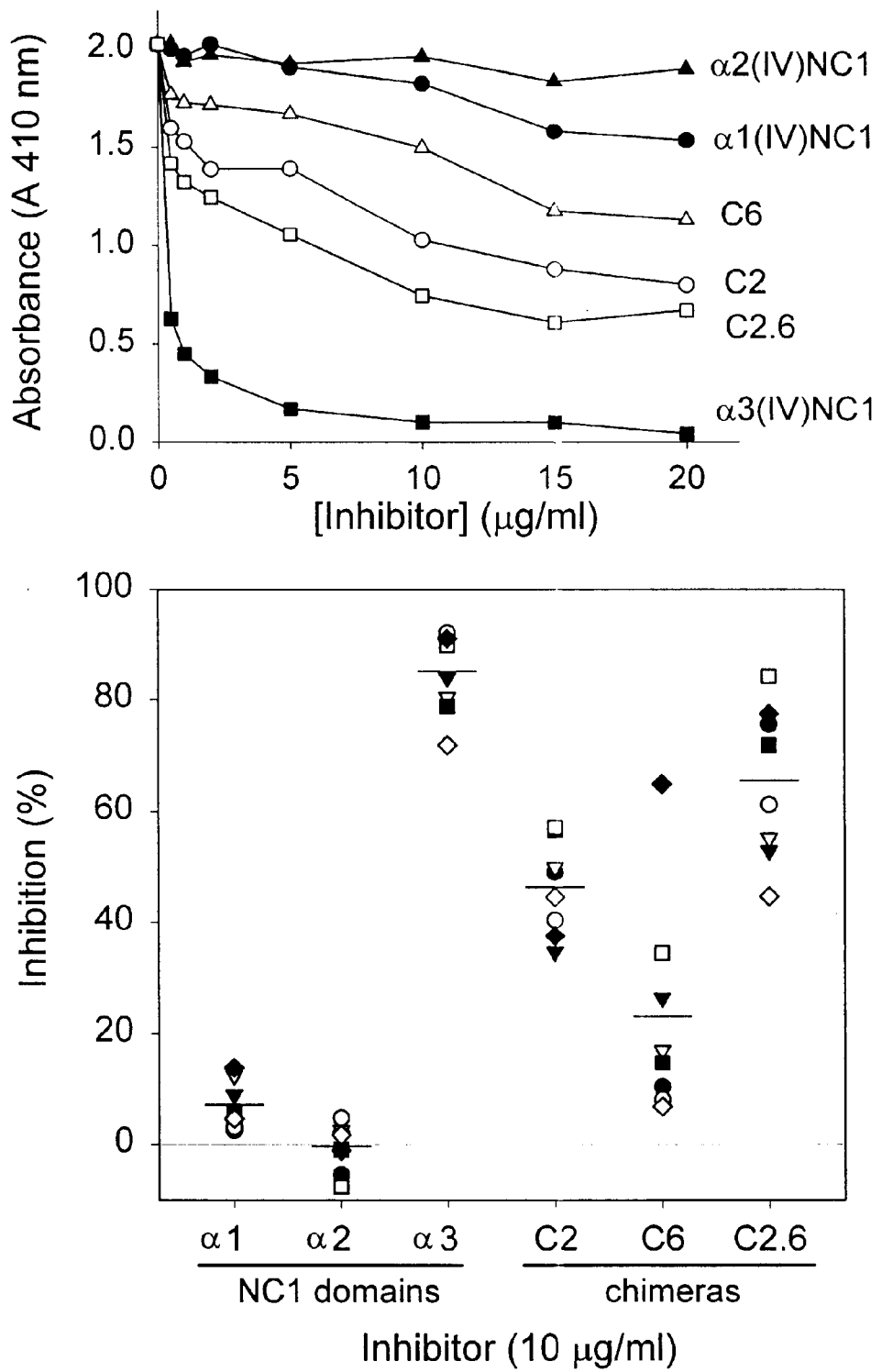

FIG. 16. Inhibition ELISA of GP antibodies binding to α3(IV)NC1 domain.

Top: Inhibition of GP-1 serum by soluble α1/α3 chimeras. The GP-1 serum, diluted 1:100, was incubated overnight with C2 (open circles), C6 (open triangles) and C2•6 (open squares) chimeras at various concentrations before the immunoassay. Recombinant α1(IV)NC1 (filled circles) α2(IV)NC1 (filled triangles) and α3(IV)NC1 (filled squares) domains were used as controls. Bottom: Comparison of eight GP sera by inhibition ELISA using α1/α3 chimeras and α(IV)NC1 domains. Sera, diluted as described in FIG. 4, were incubated overnight with 10 μg/ml antigen. ELISA was performed in plates coated with 50 ng/well α3(IV)NC1. Individual data for the eight sera are represented by symbols, and their average is shown as a horizontal line.

FIG. 17. Relative immunoreactivity against various α3(IV)NC1 regions in eight Goodpasture sera.

FIG. 18. Effect of reduction on the GP reactivity of α1/α3 chimeras.

The microtiter plates were coated with 200 ng/well native (hashed bars) or reduced (black bars) antigen in coating buffer. The proteins were reduced by treatment with 10% β-mercaptoethanol prior to immobilization. Recombinant α1- and α3(IV) NC1 domains were also used as controls. ELISA was performed using GP-1, GP-2 and GP-6 sera at 1:100 dilution.

FIG. 19. PEPSCAN analysis of the α1(IV) and α3(IV) NC1 domains.

The reactivity to α3 and α1-derived 12-mer peptides is shown by thick and thin lines, respectively. GP-1 (middle), GP-2 (top) and GP-5 (bottom) sera were used for immunoscreening at 1:50 dilution. The horizontal dotted lines are drawn two standard derivations above the median reading (continuous lines). The positions of $E_A$ and $E_B$ regions (residues 17–31 and 127–141 of α3(IV)NC1) is also shown.

FIG. 20. Comparison of α1(IV)NC1 expressed in "293" kidney cells and *E. coli.*

Microtiter plates were coated with 100 ng of native human α3(IV)NC1 purified from glomerular basement membrane (N) and recombinant α3(IV)NC1 expressed in "293" kidney cell (EK) and *E. coli* (PK), respectively. BSA-coated wells were used as a negative control Immunoreactivity with GP-1 serum was measured by direct ELISA.

DETAILED DESCRIPTION OF THE INVENTION

The present invention concerns a novel type IV collagen, α3(IV) isolated from human and bovine basement membranes. The noncollagenous (NC1) domain of α3(IV) is of particular interest as it appears to be the component of the basement membrane which reacts maximally with the Goodpasture antibody. The cloning and sequencing of a cDNA encoding 218 residues of the NC1 domain of the human α3(IV) chain, COL4A3 is described herein and will permit further study of the nature of the Goodpasture epitope. It will allow in vitro synthesis of the epitope, for use in diagnostic screening and for adsorption of pathogenic antibody for treatment of the disorder. Of further interest is the possible role of abnormalities of the α3(IV) chain in Alport syndrome, as suggested by immunological and chemical data. To determine whether α3(IV) may be mutated in Alport syndrome, applicants localized the COL4A3 gene, by somatic cell hybrid analysis and in situ hybridization of metaphase to chromosome 2. Mutations in α3(IV) cannot therefore be responsible for the vast majority of cases of Alport syndrome, which have been shown to be X-linked. One explanation for the immunochemical data is that mutations of the α5(IV) chain, which has been localized to Xq22 and found to be mutated in at least 3 kindreds with Alport syndrome, lead to failure to incorporate the α3(IV) chains into the multimeric structure of glomerular basement membrane.

It remains to be determined whether AS (Alport syndrome) mutations are confined to the α5(IV) chain or whether they also involve other type IV collagens as suggested by the immunochemical data. Applicants therefore cloned the gene encoding the α3(IV) chain as a step towards characterizing the Goodpasture antigen and determining the possible role of mutations of α3(IV) in Alport syndrome. Using the polymerase chain reaction (PCR) with primers derived from each end of the known 27 amino acid residue bovine α3(IV) protein sequence, a 68 bp bovine genomic fragment was amplified (Morrison et al. 1991). This fragment was then used to probe a bovine lens cDNA library and a 1.5 kb partial cDNA clone obtained. This encodes 238 residues of the triple helical collagenous domain and all 233 residues of the NC1 domain of the α3(IV) chain. As described here, this bovine cDNA clone was used to screen a human kidney cDNA library and a 2.7 kb human cDNA clone obtained. The clone encodes 218 residues of the NC1 domain and a portion of the 3' untranslated region of the human α3(IV) chain. Applicants have mapped this gene using somatic cell hybrids and by in situ hybridization. These techniques localize the COL4A3 gene to chromosome 2. Clearly, as the majority of cases of Alport syndrome are X-linked, mutations in COL4A3 cannot be responsible for the disorder in these patients. A mechanism whereby mutations in COL4A5 could lead to a failure to incorporate the α3(IV) chain into heterotrimers and hence into the 3-dimensional structure of basement membrane, is proposed.

The NC1 domains of type IV collagen can be excised from the basement membrane by cleavage with bacterial collagenase. The excised domains exist as hexamers, which can be separated by denaturing polyacrylamide gel electrophoresis to yield a number of monomeric and dimeric species (Butkowski et al. 1985). Maximal reactivity to serum containing Goodpasture antibody resides in the subunit Mr=28,300, designated $M28^{+++}$ in human tissue or M2* in bovine tissue (Butkowski et al. 1985; Wieslander et al. 1985). This subunit has been taken to be the NC1 domain of a novel type IV collagen, α3(IV), as it has many physical features in common with the abundant α1(IV) and α2(IV) chains, yet is clearly distinct from them (Hudson et al. 1989).

Short portions of the junctional region between the collagenous and NC1 domain of the α3(IV) chain have been sequenced in both human and bovine tissue (Saus et al. 1988; Butkowski et al. 1990). Using a PCR based strategy, with primers derived from the short bovine α3(IV) peptide sequence, applicants have cloned partial cDNAs encoding the NC1 domain of the bovine α3(IV) chain (Morrison et al. 1991) and used the bovine/human homology to clone and localize the 3' end of the human α3(IV) chain.

The amino acid sequence of α3(IV) derived from the clone KMC27 will allow further investigation of the nature of the Goodpasture epitope. It will also be of value in the design of improved assays for the specific Goodpasture antibody. At present, assays for Goodpasture syndrome rely on a crude collagenase digest of GBM. This yields occasional false positive results, as patients with other forms of nephritis develop circulating antibodies to a variety of basement membrane components, secondary to other disease processes. For example, patients with IgA nephropathy develop immune complexes containing fibronectin and IgA that bind to the triple helical domain of type IV collagen (Cederholm et al. 1988); several patients with poststreptococcal glomerulonephritis have circulating antibodies against 7S domain of type IV collagen and heparan sulphate proteoglycan (Fillit et al. 1985; Kefalides et al. 1986). The sequence data given here will be used to design synthetic peptides that will specifically detect anticollagen-α3(IV). Such peptides can also be used for adsorption of the pathogenic antibody, offering a novel treatment option for Goodpasture syndrome.

Attention has also been focussed on the possible role of mutations of the α3(IV) chain in Alport syndrome. Several investigators have found that binding of Goodpasture antibody to GBM is frequently absent in patients with this disease, as determined by immunofluorescence of GBM tissue sections (Olsen et al. 1980; Jenis et al. 1981; Jeraj et al. 1983; Kashtan et al. 1986). Absent or reduced binding of a monoclonal antibody directed towards the Goodpasture antigen has also been shown in renal biopsies from 10 Alport patients (Savage et al. 1986). In addition, immunochemical and chemical evidence for the absence of the collagenase solubilized human Goodpasture antigen, M28$^{+++}$, in the GBM of 3 patients with X-lined Alport syndrome, has been obtained (Kleppel et al. 1987). Others however, report a partial, rather than complete loss of the Goodpasture antigen in GBM sections from affected individuals (McCoy et al. 1982).

There is evidence, however, that suggests that an abnormality of the α3(IV) chain may not be the primary defect in Alport syndrome. Recently the gene encoding a further novel collagen chain, α5(IV), has been cloned, mapped to the Xq22 region and found to be mutated in at least 3 to 18 kindreds with this heterogeneous disorder (Hostikka et al. 1990; Myers et al. 1990). Several investigators have reported Alport patients who, on transplantation, develop antibodies to a 26 kD protein, rather than to the 28 kD protein expected if such antibodies were targeted to the NC1 domain of the α3(IV) chain (Kashtan et al. 1986; Savage et al. 1989). The estimated size of the α5(IV) NC1 domain is 26 kD, and may well represent the target of the the post-transplantation antibodies. Kleppel et al. (1989) have shown that both a post-transplantation antibody which recognizes the 26 kD protein, and an antibody to the 28 kD protein show an identical binding pattern to the glomerular basement membrane of a female heterozygote with Alport syndrome, consistent with random inactivation of the X chromosome.

To understand the molecular pathology of Alport syndrome, one must explain why α3(IV) is not found in the GBM of patients with the X-linked form of the disease, which at least in some cases is produced by an α5(IV) mutation. One hypothesis was that the α3(IV) and α5(IV) chains are both encoded on the X chromosome, perhaps in a head-to-head arrangement such as that observed for the α1(IV) and α2(IV) genes on chromosome 13 (Poschl et al. 1988)). As we have shown here, the gene encoding the NC1 domain of α3(IV) maps to the 2xx region. Therefore, mutations in α3(IV) cannot be responsible for the majority of cases of Alport syndrome, which are clearly X-linked (Atkins et al. 1988; Brunner et al. 1988; Fliner et al. 1988). Whether mutations in the α3(IV) chain are responsible for those cases of Alport syndrome which are said to be autosomal remains to be determined.

How then can the immunological and chemical data implicating an abnormality in the α3(IV) chain in patients with X-linked Alport syndrome be explained? One hypothesis is that, in the presence of certain but not all mutations of α5(IV), the α3(IV) chain is not stably incorporated into heterotrimers, and thence into the basement membrane. If so, one would expect that a subset of α5(IV) mutations reduce or abolish the incorporation of the α3(IV) chain (and thus reactivity to the Goodpasture antibody), while others do not affect α3(IV) chain incorporation, and thus reactivity to the Goodpasture antibody is preserved. If the defect is one of stable incorporation of α3(IV) chains into heterotrimers in the presence of α5(IV) mutations, rather than an abnormality of the α3(IV) chain per se, then transcription of COL4A3 should be normal in the kidneys of individuals with X-linked Alport syndrome.

Maximal reactivity to serum containing Goodpasture antibody residues in the subunit Mr=28,300, designated M2* in bovine tissue and a similarly sized subunit, M28+++, in human tissue (Butkowski et al, (1985), *J. Biol. Chem.,* 260, 3739–3747; Wieslander et al, (1985), *J. Biol. Chem.,* 260, 8564–8570).

M2* has been isolated from bovine GBM (glomerular basement molecule) and LBM (lens basement molecule), and a short portion of the M2* peptide from LBM has been sequenced (Saus et al, (1988) *J. Biol. Chem.,* 263, 13374–13380). M2* has been taken to be the NC1 domain of a novel type (IV) collagen, α3(IV), as it is clearly distinct from the abundant α1(IV) and α2(IV) chains, and yet has many features in common with them. It exists in monomeric and dimeric forms, has a similar molecular weight and, based on immunoprecipitation studies, is an integral component of the NC1 (noncollagenous) hexamer of collagen IV. The short amino acid sequence of α3(IV) available from the collagenous/NC1 junction revealed Gly-Xaa-Yaa triplets at the amino terminus end together with 13 residues of the NC1 domain, 8 of which were identical to the residues in the same region of the α1(IV) chain.

Disclosed herein is a PCR strategy used to clone a portion of the bovine α3(IV) gene. Degenerate oligonucleotide primers complementary to each end of the short portion of the known M2* peptide sequence were used in the PCR (polymerase chain reaction) to amplify a 68 base pai bovine genomic fragment. PCR cycles were performed using a high (68° C.) annealing temperature at first, with a stepwise reduction (1° or 2° C.) in annealing temperature in subsequent cycles. In this way, although the amount of primer bound to the template during the initial amplification cycles is small, exactly complementary primer/template interactions represent a higher proportion of the total prime/template interactions than that which occurs at lower annealing temperatures. Therefore amplification of the desired target is favored. The small 68 base pair fragment thus obtained, KEM68, was then used to probe a bovine lens cDNA library. A 1.5 kb partial cDNA clone (pKEMC15) which encodes 471 amino acid residues of the bovine α3(IV) chain was obtained.

Comparative sequence analyses

Analysis of the pKEMC15 sequence reveals features common to all type (IV) collagen chains characterized to date. Within the 238 residues of the triple helical region encoded by pKEMC15 there are 3 imperfections in the regular Gly-Xaa-Yaa repeat sequence which coincide with interruptions in the corresponding regions of the α1(IV) and α2(IV) chains. In the 233 residues of the NC1 domain there are 12 conserved cysteine residues in identical positions to those in the other type (IV) collagens. There are several extended regions of sequence identity to these other chains and 71%, 61% and 70% overall homology with the human α1(IV), α2(IV) and α5(IV) chains. Therefore the results herein which provide the complete sequence of M2* and much of the collagenous domain of its parent molecule, support its previous designation as a type (IV) collagen.

Butkowski et al, (1980), J. Lab. Clin. Med., 115, 365–373, have recently sequenced a portion of the human M28+++ peptide which was obtained from collagenase digestion of human GBM. Of the 13 residues characterized by amino acid analysis, 12 are identical to the equivalent portion of the bovine sequence obtained from pKEMC15. Furthermore, the amino acid composition of the bovine α3(IV) NC1 domain predicted from the nucleotide sequence is very similar to that obtained from previous peptide sequencing of the human M28+++ fragment. This thus adds further evidence for the equivalence of the bovine M2* and human M28+++ fragments.

EXPRESSION

The general nature of vectors for use in accordance with the present invention is not crucial to the invention. In general, suitable vectors and expression vectors and constructions therefor will be apparent to those skilled in the art.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Again, control sequences, such as recognition, promoter, operator, inducer, terminator and other sequences essential and/or useful in the regulation of expression, will be readily apparent to those skilled in the art. The vectors may be modified or engineered in any suitable manner.

In general, there are a number of methods which can be used to produce the peptide and nucleotide sequences of the invention. One straightforward method is simply to synthesize the appropriate nucleotide sequence, insert it into a suitable expression plasmid, transform a suitable host, culture the host, and obtain the peptide of the invention by any suitable means, such as sonication and centrifugation.

Alternatively, fragments can be obtained by digestion with the relevant restriction enzymes, and a suitable oligonucleotide ligated to the 5'-end coding for the missing amino acids. The resulting cDNA can then be used as above.

Other suitable methods will be apparent to those skilled in the art.

Ideally, the receiving vector has a ClaI site and a SalI site for each of insertion, but blunt-end ligation, for example, may also be used, although this may lead to uncertainty over reading frame and direction of insertion. In such an instance, it is matter of course to test transformants for expression, 1 in 6 of which should be usable. Suitable vectors may be selected as a matter of course by those skilled in the art according t the expression system desired.

By transforming E. coli with the plasmid obtained, selecting the transformant with ampicillin or by other suitable means, and adding tryptophan or other suitable promoter inducer such as indoleacrylic acid, the desired protein may be expressed. The extent of expression may be analyzed by SDS polyacrylamide gel electrophoresis—SDS-PAGE (Nature, (1970), 227, pp. 680–685).

It will also be appreciated that, where another vector is used, for example, it will be equally acceptable to employ a different selection marker or markers, or an alternative method of selection, and/or to use any suitable promoter as required or convenient.

After cultivation, the transformant cells are suitably collected, disrupted, for example, sonicated, and spun-down. Disruption may also be by such techniques as enzymic digestion, using, for example, cellulase, or by shaking with an agent such as glass beads, but methods such as sonication are generally preferred, as no additions are necessary.

Conventional protein purification is suitable to obtain the expression product.

Where not specifically described herein, methods for growing and transforming cultures etc. are usually illustrated in, for example, Maniatis (Molecular Cloning, A Laboratory Notebook, Maniatis et al. [Ed's], Cold Spring Harbor Labs, NY).

Cultures useful for the invention may suitably be cultures of any living cells, and may vary from prokaryotic expression systems up to eukaryotic expression systems. One preferred prokaryotic system is that of E. coli, owing to its ease of manipulation. However, in general terms, it is preferable to express proteins intended for use in the human body in higher systems, especially mammalian cell lines. A currently preferred such systems is the Chinese Hamster Ovary (CHO) cell line. Although this system tends not to be as easy to use as the E. coli system, its advantage lies in the processing of the protein after primary sythesis. E. coli, for example, does not have the equipment to glycosylate mammalian proteins, and it is preferred to glycosylate such proteins where possible, if for no other reason than that the natural proteins are glycosylated. In certain cases, glycosylation may be of no assistance whatever, and may even hinder the protein.

Other expression systems which may be employed include streptomycetes, for example, and yeasts, such as Saccharomyces spp., especially S. cerevisiae. With current progress in research, other systems are becoming available and there is no effective limit on which system is used, provided that it is suitable. The same systems may also be used to amplify the genetic material, but it is generally convenient or use E. coli for this purpose where only proliferation of the DNA is required.

DIAGNOSTICS

Labels for use in the present invention include, substances which have a detectable physical, chemical, or electrical property. When a detectable labeling substance is introduced, it can be linked directly such as by covalent bonds or can be linked indirectly such as by incorporation of the ultimately detectable substance in a microcapsule or liposome.

Labeling materials have been well-developed in the field of immunoassays and in general almost any label useful in such methods can be applied to the present invention. Particularly useful are enzymatically active groups, such as enzymes (see *Clin. Chem.,* (1976) 22:1232, U.S. Reissue Pat. No. 31,006, and UK Pat. 2,019,408), enzyme substrates (see U.S. Pat. No. 4,492,751), coenzymes (see U.S. Pat. Nos. 4,230,797 and 4,238,565), and enzyme inhibitors (see U.S. Pat. No. 4,134,792); fluorescers (see *Clin. Chem.,* (1979) 25:353); chromophores; luminescers such as chemiluminescers and bioluminescers (see U.S. Pat. No. 4,380,580); specifically bindable ligands such as biotin (see European Pat. Spec. 63,879) or a hapten (see PCT Publ. 83-2286); and radioisotopes such as $^3H$, $^{35}S$, $^{32}P$, $^{125}I$, and $^{14}C$. Such labels are detected on the basis of their own physical properties (e.g., fluorescers, chromophores and radioisotopes) or their reactive or binding properties (e.g., ligands, enzymes, substrates, coenzymes and inhibitors). For example, a cofactor-labeled species can be detected by adding the enzyme (or enzyme where a cycling system is used) for which the label is a cofactor and a substrate or substrates for the enzyme. Such detectable molecule can be some molecule with a measurable physical property (e.g., fluorescence or absorbance) or a participant in the enzyme reaction (e.g., see above list). For example, one can use an enzyme which acts upon a substrate to generate a product with a measurable physical property. Examples of the latter include, but are note limited to, beta-galactosidase, alkaline phosphatase and peroxidase.

EXAMPLE 1

Collagen α3(IV) Hybridization Probe

A PCR-based strategy was used to generate a bovine α3(IV) hybridization probe (Morrison et al. 1991). Degenerate sense and antisense primers were designed complementary to each end of the known 27 residue amino acid sequence of the bovine α3(IV) peptide chain. These were then used in a PCR reaction to amplify a 68 bp bovine genomic fragment (KEM68). KEM68 was then used to screen a λgt11 bovine lens cDNA library (Clontech) and a 1.5 kb partial cDNA clone obtained, encoding 238 residues of the triple helical domain and all 233 residues of the NC1 domain.

EXAMPLE 2

Screening of cDNA Library

The 1.5 kb bovine cDNA clone was then used to screen an oligo-dT primed λgt10 human kidney cDNA library (Clontech), and oligo-dT primed λgt11 human kidney cDNA library and a random primed human kidney cDNA library. Of $3 \times 10^5$ clones screened in each library, or one positive clone obtained, from the human kidney cDNA library (Clontech). The secondary from this positive was eluted into 500 μl of buffer (100 mM NaCl, 8 mM $MgSO_4 7H_2O$, 50 mM TrisCl, pH7.5 and 0.01% gelatin). 2 μl of this was used as a template for PCR with primers complementary to the β-galactosidase portion at the λgt10 template. The amplified product, KMC27 was digested with EcoR1 and cloned into the EcoR1 site of pBluescript (Stratagene). The sequence was obtained using T7 polymerase (Sequenase) with T7 and T3 sequencing primers and 17-residue oligonucleotide primers designed from known sequences of the inserts, according to the standard protocols.

EXAMPLE 3

Chromosomal Assignment

Southern blot hybridization of α3(IV) probe to rodent x human hybrids.

Chromosomal assignment of the human α3(IV) gene was performed using a panel of 11 human-Chinese hamster hybrids. DNA from human and Chinese hamster parental cell lines and human x rodent hybrids was digested to completion with Pst1. The DNA was fractionated by electrophoresis on a 0.9% agarose gel and blotted onto Hybond $N^+$ (Amersham International). A 1.7 kb 5' portion of the cDNA KMC27 was labelled with [α-$^{32}$P]dCTP by random primer labelling (Feinberg and Vogelstein, 1983) and hybridized to the filter bound DNAs in Church and Gilbert buffer (0.5M $Na_2HPO_4$, 7% SDS, 1% BSA, 1 mM EDTA) at 65° C. The filters were then washed in 0.1% SDS and 1×SSC (0.5M NaCl, 0.015M Na Citrate, pH7.0) and exposed to film for 3 days.

Northern Analysis

Total RNA was isolated from snap-frozen bovine 60 day old calf tissues using an acid guanidinium thiocyanate/phenol/chloroform extraction procedure (Chomczynski and Sacchi, 1987). 5–10 μg was electrophoresed on a 1.2% agarose gel containing formaldehyde, blotted to nitrocellulose and hybridized with KEMC15, the bovine COL4A3 probe. Washing was in 0.1% SDS, 0.5×SSC at 65° C. and the filter exposed to film for 2 days. $pA^+$ RNA was isolated from total RNA using an oligo dT column (Collaborative Research Inc, Waltham, Mass.).

EXAMPLE 4

Isolation of cDNA Clones

To generate an α3(IV) hybridization probe, use was made of the 27 residue amino acid sequence of the bovine α3(IV) chain, as no human α3(IV) amino acid sequence was currently available (Saus et al. 1988). The polymerase chain reaction was used to amplify a 68 bp segment corresponding to the bovine sequence. A longer bovine cDNA clone (KEMC15) was then obtained from a bovine line library. KEMC15 encodes 238 residues of the triple helical region and the complete 233 residues of the NC1 domain. Applicants anticipated that the bovine and human α3(IV) amino-acid sequences would be highly conserved in this region (Butkowski et al. (1990) have subsequently shown conservation of eleven residues in a twelve residue stretch). Therefore applicants used the bovine clone to screen for human homologs. On screening $3 \times 10^5$ clones of each of 3 human kidney cDNA libraries with KEMC15, only 1 positive clone, KMC27, was obtained.

EXAMPLE 5

Nucleotide Sequence of α3(IV) cDNA

Sequence analysis of the cDNA clone KMC27 reveals an open-reading frame which, on translation, encodes 220 carboxy terminal residues of the NC1 domain of α3(IV) and ~2000 bp of the 3' untranslated region. As anticipated, within the coding region, the bovine and human sequences are very similar, with 90.5% homology at the nucleotide level and 93% homology at the amino acid level. Only 2 of the 15 non-identical amino acid residues are non-conservative substitutions. The homology of the sequence encoded by KMC27 with the bovine COL4A3 sequence, confirms its identity as a portion of the human COL4A3 gene. The amino acid composition of the NC1 domain of α3(IV) derived from the sequence of KMC27 is similar to that obtained from amino acid composition analysis of the human $M28^{+++}$ fragment (Butkowski et al. 1990).

EXAMPLE 6

Comparative Sequence Analysis analysis of pKMC27 reveals features common to all type IV collagens characterized to date. In the 220 residues of the NC1 domain there are 12 conserved cysteine residues in identical positions to those in the other type IV collagens. Overall the sequence shows 71%, 60% and 70% amino acid identity with the NC1 domains of the human α1(IV), α2(IV) and α5(IV) chains respectively.

It has been suggested that the NC1 domains of α1(IV) and α2(IV) are the result of an intragenic duplication, as each consists of two equal-sized internal repeats, each containing 6 cysteine residues in invariant positions (Brinker et al. 1985; Pihlajaniemi et al. 1985; Myers et al. 1987). In the α1(IV) NC1 there are 45 (out of 229) positions in which the amino acid is identical between the two halves (Brinker et al. 1985; Pihlajaniemi et al. 1985) compared with 50 positions in the α2(IV) NC1 (out of 230) and 43 in the α5(IV) NC1 (Pihlajaniemi et al. 1990). Alignment of the corresponding internal repeats in the α3(IV) chain shows that 45 amino acids are conserved between the putative duplicated halves of the NC1 domain, including all twelve cysteine residues. Of the 116 amino acid residues conserved between all 4 chains, 62 are also conserved between the 'duplicated halves' of the NC1 domain in duplications.

As Dion and Myers (1985) have speculated, the conserved elements may play a role in the assembly of triple helical molecules, while the variable regions may be operative in discriminate chain selection. This may aid in the search for that portion of the α3(IV)NC1 responsible for the Goodpasture epitope. Comparing the last 219 residues of the NC1 domains of α1(IV), α2(IV), α3(IV) and α5(IV), there are 46 positions in which the sequence of only one chain differs from the other 3; of these 46, 3 are a divergence of the α1 chain, 26 are a divergence of the α2 chain, 16 are a divergence of the α3 chain and one a divergence of the α5 chain alone. None of these divergences is duplicated, suggesting that intragenic gene duplication to form a complete NC1 domain preceded the evolution of the different type IV collagen chains.

EXAMPLE 7

Chromosomal Localization

Human x Rodent Somatic Cell Hybrids

To localize COL4A3, a panel of Chinese hamster x human somatic cell hybrids was analysed by Southern blot hybridization with a portion, KMC17, of the human KMC27 cDNA, as a probe. The results are shown in FIG. 3. KMC17 detects a band of 11 kb in the Chinese hamster DNA and a band of 9 kb in the human DNA. The panel shown maps KMC17 to chromosome 2.

In Situ Hybridization

The α3(IV) gene was independently mapped by in situ hybridization of the KMC17 cDNA clone to human metaphase chromosomes.

Northern Analysis

The bovine cDNA clone KMC15 which encodes 471 residues of the bovine α3(IV) chain, was used to probe a Northern blot of total RNA from bovine lung, liver and kidney. The gene codes for a single transcript of approximately 8.1 kb, the signal being equally intense in total RNA from lung and kidney, but absent in liver. Using 10 μg of polyA$^+$ selected RNA a similar result was obtained, with similar intensity of hybridization in lung and kidney and a very faint signal obtained from liver RNA (data not shown). This is compatible with the observation that patients with Goodpasture syndrome show pathology in the lung and kidney, but no discernible liver abnormality.

EXAMPLE 8

Determination of the Molecular Structure of the GP-autoantibody Combining Site (Epitope)

The epitope which reacts with GP-antibodies resides on monomeric and dimeric forms of the NC1 domain of the α3 chain of type IV collagen. The epitope contains a critical disulfide bond that is required for binding of GP antibodies. Knowledge of the epitope structure will yield information required for the development of diagnostic procedures for the detection of GP antibodies and development of therapeutic procedures for the removal of the toxic GP antibodies from blood plasma.

In applicants' search for the molecular identity of the GP epitope, applicant have employed mild chemical modification with a biotinylating reagent (sulfosuccinimidyl 6-biotinamido hexamoate [NHS-LC-Biotin]) which is highly specific for lysine and N-terminal amino acid residues. Lysine was selected because of the important role played by reactive amino groups in protein structure that ultimately dictates immunogenicity. The D2 fraction of NC1 hexamer, comprised of dimeric subunits reacting with GP-antibodies were biotinylated with the reagent and the produces were analyzed by Western blotting with GP-sera (FIG. 1). Biotinylation abolished the reactivity of the dimeric subunits with GP sera. These results indicate that lysine is a critical residue of the epitope structure.

Applicants also inventigated the influence of carboxypetidase treatment on the reactivity of the dimer subunits with GP sera. As shown in FIG. 2, this treatment also abolished reactivity with GP sera. These results suggest that the carboxy terminus is an important element of the epitope structure.

In addition to these structural features (disulfide bond, lysine, and carboxy terminus), the epitope is expected to be distinct in amino acid sequence from an analogous region of the other known chains (α1, α2, & α5) of type IV collagen and to likely have a hydrophilic character. Based on molecular cloning studies, a region at the carboxy terminus of the NC1 domain of the α3 chain was identified that fits these five criteria. Its structure for human α3 is:

— — — — —ISRCQVCMKKRH

This 12 Mer peptide was chemically synthesized with the two cysteine residues blocked. The peptide was tested with ELISA measurements, as shown below, and found to be reactive with GP antibodies.

EXAMPLE 9

Reactivity of α3 Synthetic Peptide with GP Antibodies

The reactivity was tested with anti sera from two GP patients using two different inhibition ELISA procedures. In FIG. 3, the peptide was preincubated with GP antibodies for 12 hours and the mixture then reacted with authentic GP antigen (α3 NC1 bovine monomer). The results show 60% inhibition at saturation (peptide concentration=5.4 10-6 molar). This information suggests that the peptide binds the GP antibody and thus represents a portion of the native epitope.

The reactivity of the peptide was also tested by another procedure where the peptide was allowed to compete with the GP antigen for binding with GP antibodies for 12 hours. The results show 42% inhibition. As control, N-terminal peptides (10 Mer) from α1, α2, α3, & α4 NC1 domains were tested for reactivity, and the results showed no inhibition. These results further indicated that the α3 carboxy terminal peptide uniquely binds the GP antibody.

Figure 4:
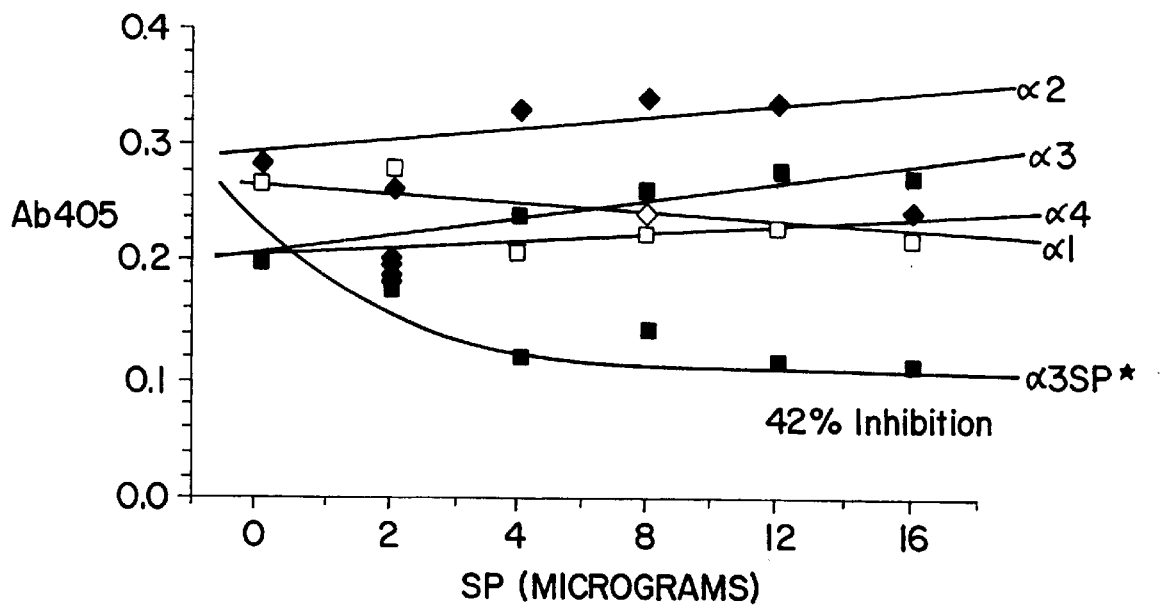

Overall, these ELISA results indicate that the α3 carboxy terminal peptide represents a portion of the native epitope (see FIG. 4).

EXAMPLE 10

Figure 5:
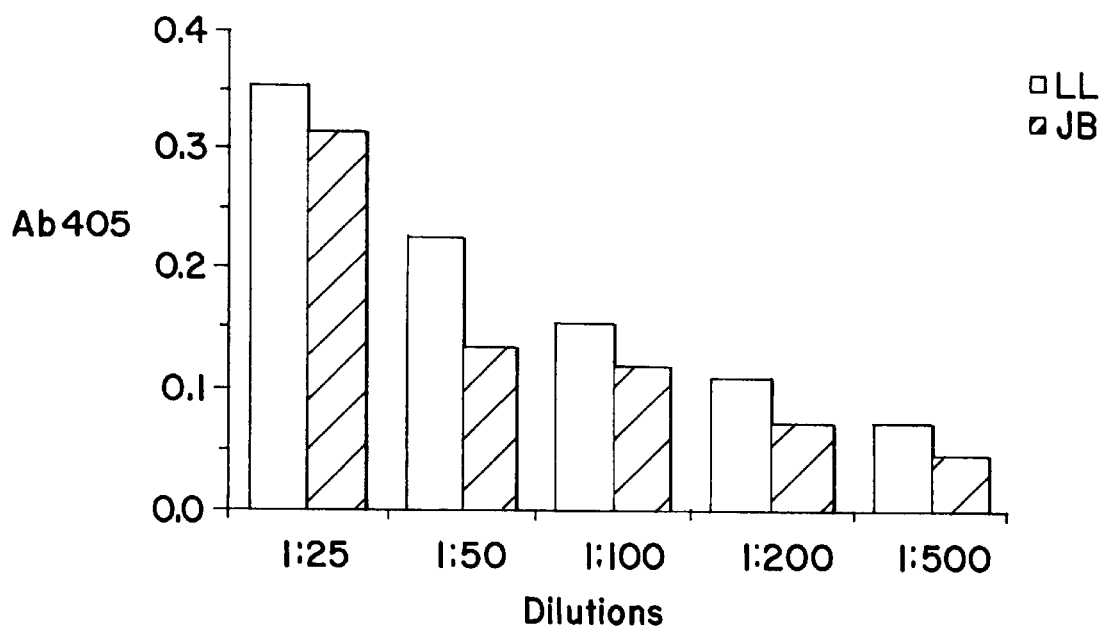

Development of Diagnostic Procedure for the Detection of GP Antibodies in Human Sera The α3 carboxy terminal peptides was allowed to bind to ELISA plates and tested for reactivity with GP antibodies using a direct ELISA procedure. Using two GP seras, as shown in FIG. 5, the peptide bound antibody in a dose dependent manner. This indicates that the peptide can be used as a diagnostic tool for the detection of GP antibodies in blood plasma.

EXAMPLE 11

Development of a Therapeutic Procedure for the Removal of GP Antibodies from Blood Plasma The α3 carboxy terminal peptide was bound to cyanogen bromide activated Sepharose 4B column. The column was then tested for specific binding of GP antibodies from sera. The bound antibodies were eluted and tested for reactivity with GP antigen by Western blotting (FIG. 6). The results show distinct reactivity with the GP antigen. This indicates that the peptide can be used to prepare a immunoabsorbent column to selectively remove toxic antibodies from blood plasma of patients with GP syndrome.

EXAMPLE 12

Primer Design for the Generation of Collagen α3 (IV) Hybridization Probes

Two PCR based strategies were used to generate hybridization probes. Both made use of the known 27 residue amino acid sequence of the bovine α3(IV) chain. Firstly, four degenerate sense primers (17–22 mers) were designed corresponding to regions of the known bovine α3(IV) sequence that were most distinct from the corresponding α1(IV) and α2(IV) sequences (FA,FB,FC,FD). Antisense primers were then designed to be complementary to regions of the NC1 that are highly conserved between the human and mouse α1(IV) and α2(IV) chains, in anticipation that such homology would extend to the α3(IV) chain (RA,RB,RC, RD). The second strategy involved using degenerate (32-fold) sense primers (17 mers), corresponding to the amino acids near the amino terminal end of the known 27 residue sequence of bovine α3(IV) (F1,F2,F3,F4). Similarly degenerate oligonucleotide antisense primers were also designed, corresponding to the amino acids at the carboxyl end of the known sequence (R1,R2,R3,R4) (FIG. 7).

EXAMPLE 13

PCR Protocols

Standard PCR reactions were performed in a 50 μl volume containing 10–20 ng of either bovine genomic, human genomic or human cDNA template, 25 pmols of each oligonucleotide primer, 200 μM of each dNTP, 50 mM KCl, 10 mM Tris (pH 8.3), 1.5 mM $MgCl_2$, 0.01% gelatin and 1.25 units of Taq polymerase (Perkin Elmer Cetus). Samples were overlaid with 50 μl mineral oil. Routinely, 35 cycles of PCR were performed. With primers FA–FD and RA–RD, annealing was performed at 60° C. for 1 minute, extension at 72° C. for 2 minutes and denaturation at 94° C. for 1 minute, with a final extension time of 10 minutes. With primers F1–F4 and R1–R4, annealing was for 30 seconds at 68° C. for the first cycle, at 66° C. for 30 seconds for the second, at 64° C. for 30 seconds for the third and at 58° C. for the fourth and subsequent cycles. No extension step was performed as the predicted product was only 68 base pairs. Denaturation was carried out at 94° C. for 1 minute.

EXAMPLE 14

Subcloning and Sequencing

The 68 bp product obtained using primers F4 and R3 and bovine genomic template (KEM68) was cloned into the EcoRV site of the phagemid pBluescript II (Stratagene). The double-standard plasmid, pKEM68, was sequenced using T7 polymerase (Sequenase) with T7 and T3 sequencing primers according to standard protocols.

EXAMPLE 15

Screening of cDNA Library

KEM68 was labelled by PCR. A 50 μl reaction was performed containing 5 pmoles of primers F3 and R4, 50 pg of pKEM68, 10 μM dATP, dGTP, dTTP and 9.4 μM dCTP. 10 μl of [α-$^{32}$P]dCTP (3000 Ci/mmol) was added to give a final concentration of 0.6 μM. Standard buffer and 1 unit of Taq polymerase were used and 30 cycles of amplification performed. The reaction product was passed through a G25 column to remove most of the unincorporated primers. The labelled product was used to screen a λgt11 bovine lens cDNA library (Clontech). A total of $3\times10^5$ clones were screened and 16 positives obtained. Secondaries from these positives were eluted into 500 μl of buffer (100 mM NaCl, 8 mM $MgSO_4 7H_2O$, 50 mM TrisCl, pH 7.5 and 0.01% gelatin). 2 μl of eluant was used as a template for PCR with primers complementary to the 62 -galactosidase portion of the λgt11 template. The largest of the 16 amplified products, KEMC15, was sequenced directly using the same λgt11 primers as in its initial amplification. KEMC15 was subsequently cloned into the EcoRV site of pBluescript II (Stratagene). The complete sequence was obtained using 17-residue oligonucleotide primers designed from known sequences of the insert (FIG. 9).

EXAMPLE 16

Collagen α3(IV) Hybridization Probe

The known 27 residue amino acid sequence of the junction between the collagenous and NC1 domains of bovine α3(IV) was used to generate an α3(IV) hybridization probe (Saus et al, (1988) *J. Biol. Chem.,* 263, 13374–13380). As the number of nucleotide sequences that may encode this peptide segment is very large, highly degenerate oligonucleotide probes would be required to include all coding possibilities. Consequently, two PCR based strategies were adopted.

In the first approach, primers were designed to correspond to regions of the known 27 amino acid sequence of bovine α3(IV) that is most distinct from the corresponding portion of α1(IV) and α2(IV) (FA–FD). On this basis, the most suitable sense primers corresponded to the carboxy terminal region of the known sequence, allowing no room for an antisense primer to be designed complementary to the known residues. Therefore, use was made of the number of highly conserved stretches of 6–7 amino acids in the NC1 domain of α1(IV) and α2(IV), which are also conserved between species. If such sequences represent essential structural elements of type (IV) collagen, it might be assumed that such homology would extend to α3(IV). 17–20mers (RA–RD) complementary to portions of these conserved regions were therefore designed. Where α1(IV) and α2(IV) differed in these regions, a degenerate oligonucleotide was synthesized. By intention, the maximum degeneracy of these antisense primers was only 4-fold. Using various combinations of primers FA–FD and RA–RD and standard PCR protocols, products of the "correct" size were obtained using a human cDNA template, and discrete products of various sizes obtained using either human or bovine genomic templates. However, sequence analysis of these products revealed them to be portions of genes encoding α1(IV), or α2(IV).

A second strategy was therefore adopted which did not rely on the assumed homology of regions of the NC1 domain of α3(IV) with α1(IV) and α2(IV). In this approach, sense and antisense primers were designed complementary to each end of the known 27 amino acid protein sequence. As the peptide sequence is so short, there was little latitude in the design of these primers. The 3' ends of the primers had to be as distinct as possible from the corresponding regions of α1(IV) and α2(IV), to avoid amplification of these known collagen genes. Four sense primers, F1–F4, were synthesized according to the amino acid sequence lys-pro-gly-asp-thr-gly, near the amino terminal end of the known sequence. AAG was used for lysine, based on codon usage frequencies in collagens. All codons for proline, glycine and asparagine were included. Four separate sense primers were synthesized, each using a different nucleotide as the wobble base of threonine, to eliminate degeneracy from the five nucleotides at the 3' end of the primers. Antisense primers were synthesized complementary to the amino-acid sequence tyr-his-arg-phe-ala-val-phe, near the carboxy terminus of the peptide sequence. Again, four primers were made to eliminate degeneracy from the five 3' most nucleotides. Two of the primers (R1 and R2) incorporated the complement of the codons CG(A/C/G/T) for arginine, and two (R3 and R4), the complement of AG(A/G) for arginine (FIG. 7).

Standard 3-step PCR protocols (denature, anneal, extend) and combinations of the degenerate primers F1–F4 and R1–R4 did not yield an amplification product of the correct (predicted) size from a bovine or human genomic template or human cDNA template. The use of degenerate primers precludes the calculation of a specific predicted annealing temperature and therefore, experiments were performed with a range of annealing temperatures. Despite the use of stringent annealing temperatures and short (15 sec) annealing times, in practice many products of up to 2000 base pairs in size were generated. In an attempt to reduce the complexity of the PCR products, a PCR cycling profile with stepwise reductions in annealing temperature were adopted. The goal of the stepwise protocol is to reduce spurious amplification products during early cycles. Once a double-stranded product was has been formed by PCR, regardless of the match between primer and template, that product is a perfect template for primer annealing in subsequent cycles. The use of high initial annealing temperatures reduces spurious binding of primer and increases the proportion of correct annealing, but does so at the expense of the efficiency of generation of 'correct' product. After early cycles of stringent amplification have increased the proportion of desired product in the mix, subsequent reduction of the annealing temperature allows a more efficient amplification to occur.

Figure 8A:
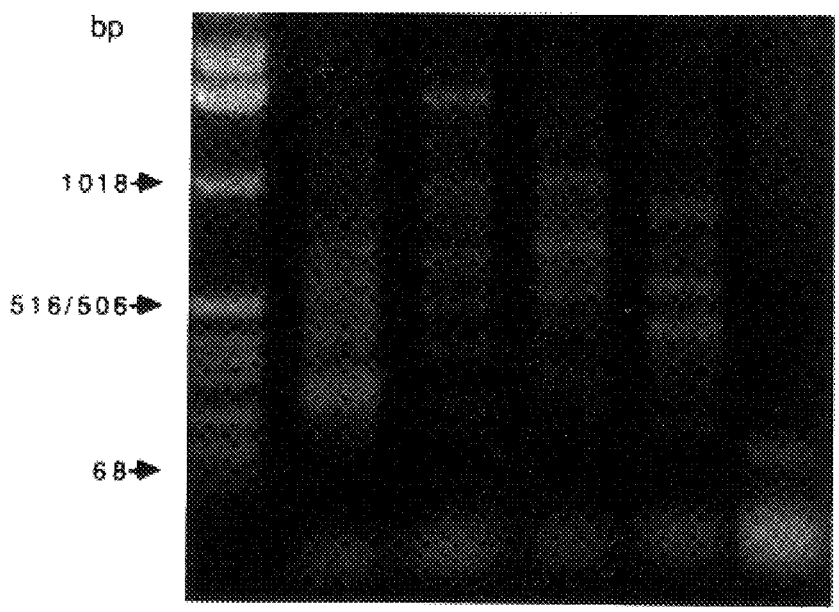
Figure 8B:
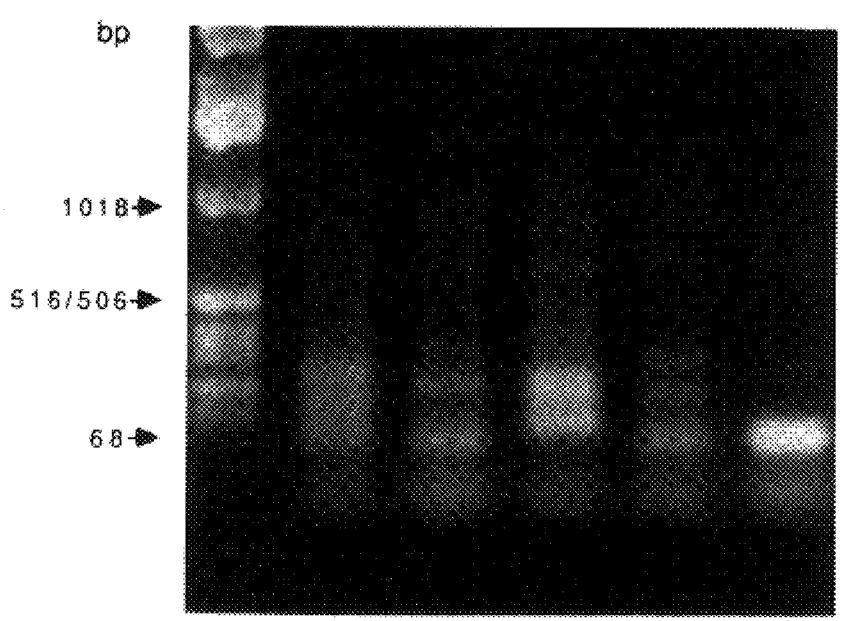

FIG. 8a shows an example of the PCR products obtained using combinations of the primers F1–F4 and R3, using a standard PCR cycling profile. No product of 68 base pairs is evident in any of the reactions using the degenerate primers. As FIG. 8b shows, by reducing the annealing temperature in a stepwise fashion, a 68 base pair product is clearly obtained when primers F2 and R3 or F4 and R3 are used. For non-degenerate primers, such as F9* and R9*, which are exactly complementary to portions of α1(IV), the "correct" product is obtained using both cycling profiles.

EXAMPLE 17

Nucleotide Sequence of α3(IV) cDNA

Figure 9:
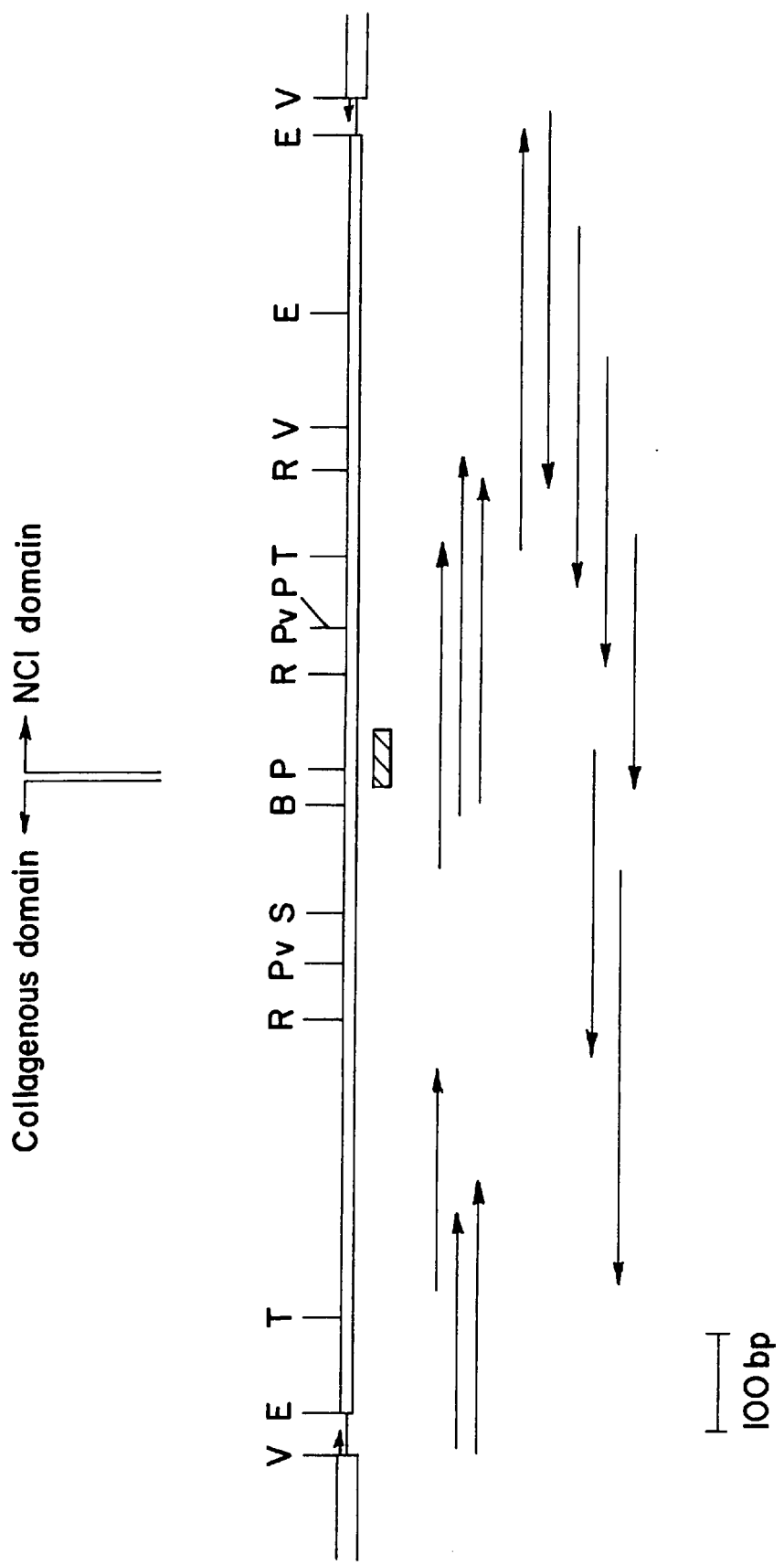

The 68 base pair fragment obtained using primers F4 and R3 and bovine genomic template, KEM68, was then cloned. Sequence analysis of pKEM68 revealed an open reading frame which, on translation, codes for a peptide sequence identical to the known peptide sequence of α3(IV). A bovine lens cDNA library was then screened with KEM68 yielding 16 positive clones of 0.5–1.5 kb. A partial restriction map of the longest clone, pKEMC15, is shown in FIG. 9. DNA sequencing of pKEMC15 showed that the clone codes for the known α3(IV) amino acid sequence with the exception of a serine-for-tyrosine substitution at the 15th amino acid of the NC1 domain. Subsequently, Gunwar et al, (1990), *J. Biol. Chem*, 265, 5466–5469 have published a second partial amino acid sequence of α3(IV) in which a serine was also found at position 15. Furthermore, an additional four amino acids were obtained by Hudson et al and these were the same as the amino acids predicted from the nucleotide sequence of clone pKEMC15.

pKEMC15 encodes all of the NC1 domain as well as 238 amino terminal residues of the collagenous repeat sequence Gly-Xaa-Yaa and 8 base pairs of the 3' untranslated region. Table 1 shows the amino-based composition of NC1 α3(IV) derived from the sequence of pKEMC15 compared to that obtained from amino acid analysis of bovine M2* and human M28$^{+++}$.

TABLE 1

Comparison of amino acid compositions of collagenase-resistant fragments from basement membrane with the composition of the bovine α3(IV) NC1 domain predicted from nucleotide sequence.

| | Number of residues | | |
|---|---|---|---|
| Amino acid | α3(IV) | M2* | M28$^{+++}$ |
| Alanine | 20 | 18.5 | 19.2 |
| Phenylalanine | 15 | 14.1 | 16.9 |
| Lysine | 5 | 4.7 | 6.2 |
| Proline | 20 | 21.7 | 17.7 |
| Threonine | 15 | 14.7 | 19.3 |
| Cysteine | 12 | NE | NE |
| Glycine | 19 | 24.9 | 22.5 |
| Leucine | 15 | 17.1 | 18.2 |
| Glutamine/Glutamic acid | 19 | 21.3 | 20.6 |
| Valine | 8 | 9.2 | 10.4 |
| Asparagine/Aspartic acid | 14 | 14.2 | 14.5 |
| Histidine | 4 | 5.2 | 6.6 |
| Methionine | 9 | 7.3 | 3.0 |
| Arginine | 12 | 12.1 | 14.1 |
| Tryptophan | 4 | NE | NE |
| Isoleucine | 14 | 10.7 | 11.1 |
| Serine | 23 | 21.4 | 18.5 |
| Tyrosine | 7 | 6.9 | 6.2 |

Composition of M2* is from Butkowksi et al, (1985), J. Biol. Chem., 260, 8564–8570. Composition of M28+++ is from Butkowski et al (1980), J. Lab. Clin. Med. 115, 365–373. NE: no amino acid determination made.

EXAMPLE 18

Comparative Sequence Analysis

The deduced amino acid sequence reveals several features typical of type IV collagens. The NC1 domain is similar in length to α1(IV), α2(IV) and α5(IV) and contains 12 cysteine residues in identical places. Regions that are highly conserved between α1(IV), α2(IV) and α5(I) are also highly conserved in α3(IV). The three imperfections in the Gly-Xaa-Yaa repeat sequence found in the 238 residues of the triple helical region abutting the NC1 domain in α3(IV) occur at identical points of the collagenous domain in human α1(IV), α2(IV) and α5(IV). Overall the sequence shows 71%, 60% and 70% amino acid identity with the NC1 domains of the human α1(IV), α2(IV) and α5(IV) chains.

It will be appreciated that the instant specification is set forth by way of illustration and not limitation, and that various modifications and changes may be made without departing from the spirit and scope of the present invention.

EXAMPLE 19

Mapping the Major Conformational Goodpasture Autoepitopes

In this example, chimeric proteins were used to map the location of the major conformational, disulfide-bond dependent Goodpasture (GP) autoepitope(s) that has been previously localized to noncollagenous (NC1) domain of α3(IV) chain. Fourteen α1/α3 NC1 chimeras were constructed by substituting one or more short sequences of α3(IV)NC1 at the corresponding positions in the non-immunoreactive α1(IV)NC1 domain and expressed in mammalian cells for proper folding. The interaction between the chimeras and eight GP sera was assessed by both direct and inhibition ELISA. Two chimeras, C2 containing residues 17–31 of α3(IV)NC1 and C6 containing residues 127–141 of α3(IV) NC1, bound autoantibodies, as did combination chimeras containing these regions. The epitope(s) that encompasses these sequences is immunodominant, showing strong reactivity with all GP sera and accounting for 50–90% of the autoantibody reactivity toward α3(IV)NC1. The conformational nature of the epitope(s) in the C2 and C6 chimeras was established by reduction of the disulfide bonds by PEPSCAN analysis of overlapping 12-mer peptides derived α1- and α3IV)NC1 sequences. The amino acid sequences 17–31 and 127–141 in α3(IV)NC1 have thus been shown to contain the critical residues of one or two disulfide bond-dependent conformational autoepitopes that bind GP antibodies.

Introduction

The GP autoepitope(s) has been localized to the NC1 domain of the α3(IV) chain (5,6). Antibodies that bind to the NC1 domain of other α(IV) chains may be found in some Goodpasture patients (7,8), but they only account for about 10% of autoreactivity (9). The autoepitope(s) in the α3(IV) NC1 domain appears to be conformational, because reduction of disulfide bonds abolishes most of the binding (9–11). The identification of the precise amino acid residues that constitute this epitope(s) is important for understanding the etiology and pathogenesis of the GP disease and for the development of diagnostic and therapeutic agents. Several groups have attempted to map the location of the autoepitope(s) by using short linear peptides (9,11–14) or by site-directed mutagensis of the α3(IV)NC1 domain expressed in *E. coli* (15). Although linear sequences have been identified that bind GP antibodies, these findings are at variance with each other. Moreover, prior studies have not addressed whether these linear sequences constitute the major conformational, disulfide bond-dependent epitope(s).

The aim of these experiments was to identify the α3(IV) NC1 amino acid sequences that form the thus far elusive conformational GP epitope(s). To circumvent the limitations of previous approaches, we pursued an epitope mapping strategy based on chimeric proteins. This approach has been specifically developed and successfully used to map conformational epitope(s) (16) or autoepitopes (17). We hypothesized that α3(IV)NC1 regions most likely to form the autoepitope(s) are those most divergent from the other homologous α(IV) chains. A series of chimeric α1/α3(IV) NC1 domains were constructed in which these candidate α3(IV)NC1 sequences replaced the corresponding sequences in the non-immunoreactive α1(IV)NC1. The chimeras were expressed in mammalian cells for correct protein folding and disulfide bond formation. We report that two specific sequences, α3(I)NC1 residues 17–31 and 127–141, contain the critical residues of one or two disulfide bond-dependent conformational GP autoepitopes within the α3(VI)NC1 domain.

EXPERIMENTAL PROCEDURES cDNA manipulation and chimera construction

Figure 10:
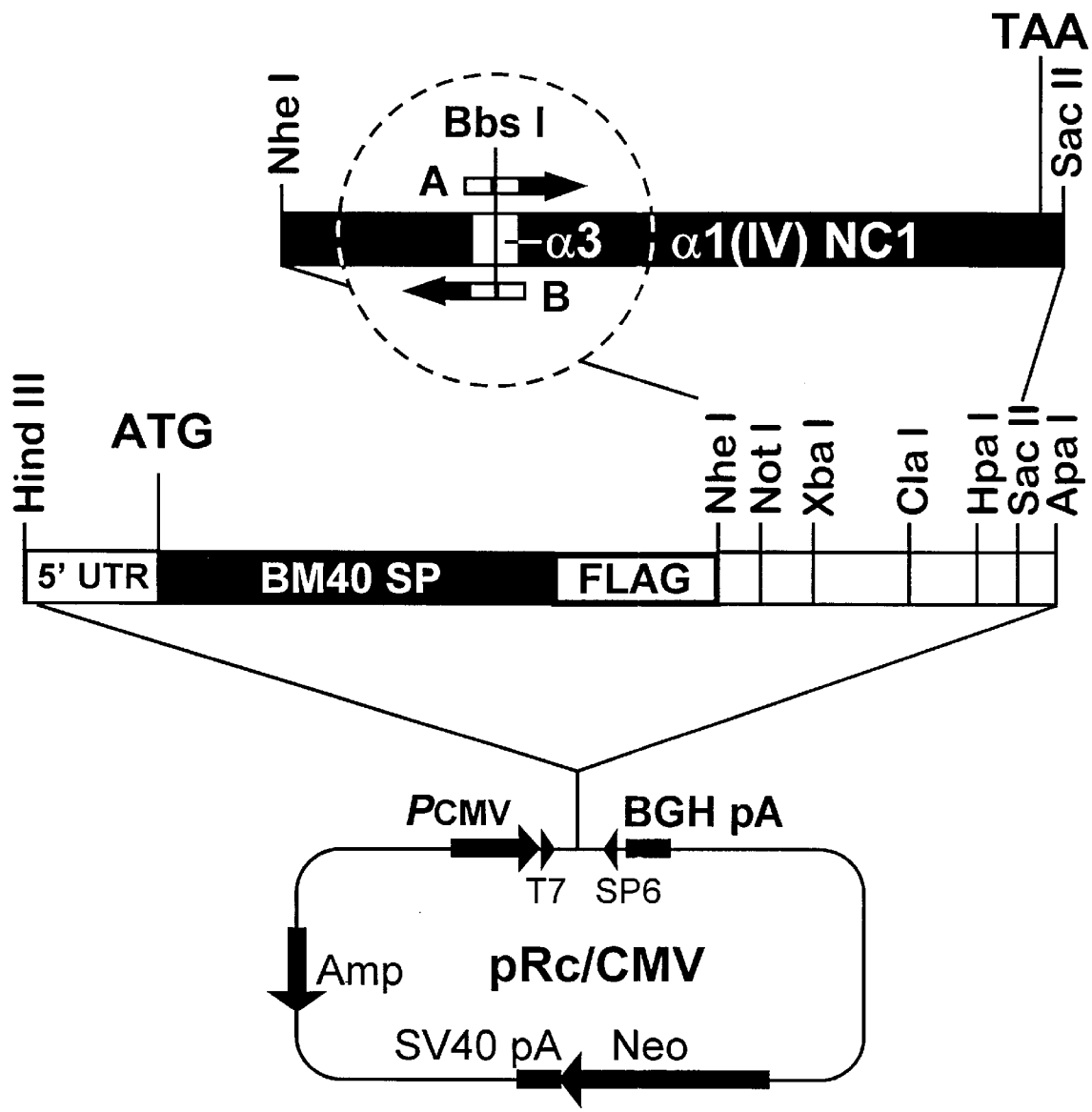

A suitable vector (FIG. 10) for the expression of recombinant proteins was based on pRc/AC7, a derivative of pRc/CMV (Invitrogen) that contained and expression cassette consisting of the BM-40 5' untranslated region, BM-40 signal peptide, and an α3 type VI collagen insert (18). By using a two-step inverse PCR with the appropriate primers (FIG. 11), the original insert was replaced by a FLAG™ recognition sequence (Kodak), and additional restriction sites (NheI, ClaI, HpaI, and SacII) were introduced further downstream. The resulting vector (pRc-X) was used for the expression of the chimeras (FIG. 10, middle). After cleavage of the signal peptide, secreted proteins would contain at the amino terminus a 14-residue fusion sequence (APLA DYKDDDDKLA) that included the FLAG peptide (underlined) used for affinity purification.

The cDNA for the human α1(IV)NC1 domain was amplified from a human kidney cDNA library (Marathon-Ready™, Clontech) by PCR using Klentaq polymerase (Clontech) and subcloned into pCR™II vector by using a TA cloning kit (Invitrogen). The inserts with the correct sequence were subcloned into pRc-X. The resulting pRc/fα1 construct was subsequently used for the construction of α1/α3 chimeras (FIG. 12). Unless otherwise indicated, Pfu polymerase (Stratagene) was used in the PCR reactions for its low error rates. Restriction enzymes and ligase were purchased from New England Biolabs. The correct sequence of each construct was verified by sequencing The principle of the inverse PCR approach that was used for chimeras C2, C3, C5, and C6 is depicted inside the dashed circle in FIG. 10 (top). The primers (FIG. 11) were designed in a back-to-back orientation, each containing (in 3'to 5' order) residues complementary to the α1(IV) NC1 template, residues complementary to a part of the replacement α3(IV) NC1 sequence, and the recognition site of the inward-cutting BbsI restriction enzyme (GAAGAC(N)2/6). PCR yielded 6.3 kb amplicons that comprised the whole vector and insert. Digestion with BbsI removed the recognition site and created complementary ends inside the inserted α3(IV) sequence, then ligation produced a circular expression vector containing a chimeric α1/α3(IV)NC1 insert with no extraneous sequence.

Construction of C1 and C4 chimeras was based on a regular PCR strategy using pRC/fα1 as a template and introducing α3 sequences by primers at the 5' and 3' ends of the NC1 insert, respectively. The PRC products were digested with restriction enzymes (FIG. 11 and subcloned into the pRc-X vector for expression. The construction of C7 chimera followed a similar scheme, requiring C1 as template. In order to construct chimera C8, two collagenous Gly-X-Y triplets of the α1(IV) chain had first to be added to the 5' end of the α1(IV) NC1 sequence. An α1(IV)NC1+ Gly-X-Y insert was amplified from a pRc/fα1 template, digested with NheI/PpuMI and ligated into a C3–4 vector preparation cut with the same enzymes. Inverse PCR with this template generated chimera C8.

Six combination chimeras were also constructed: C1•2, C1•4, C2•6, C3•5, C1•2•5, and C7•8, C1•2 chimera was generated using primers for the C1 construct and C2 as template, digested with NheI and ClaI, and then subcloned into the pRc-X vector. The remaining chimeras were generated by subcloning the chimeric insert region of one chimera into a vector preparation of another chimera digested with the same restriction enzymes. C1•4 required subcloning of a NheI/PpuMI C1 insert fragment into the C4 vector, likewise, C2•6 required an ApaI C6 insert in the C2 vector; C3•5 required a PpuMI/SacII C3 insert in the C5 vector; C1•2•5 required an ApaI C5 insert in the C1•2 vector; and C7•8 required a PpuMI/SacII C8 insert in the C7 vector.

Protein expression and purification.

Recombinant α1/α3 chimeras were expressed in human embryonic kidney 293 cells (ATCC 1573-CRL) grown in DMEM/F12 medium (Sigma) supplemented with 5% fetal bovine serum (Sigma) and 50 µg/ml ascorbic acid phosphate (Wako). Five to ten µg of plasmid DNA were transfected by the calcium phosphate co-precipitation method (10) into 70% confluent 293 cells. After two days, transfected cells were selected with 250 µg/ml G418 (Gibco). Resistant cells were screened for expression of recombinant protein by Western blot using an anti-FLAG monoclonal antibody (M2, Kodak) and expanded for quantitative expression. The medium was collected from subconfluent cultures every 48 h and the recombinant proteins were purified by affinity chromatography or anti-FLAG M2 affinity columns (Kodak) according to the manufacturer's instructions. Protein solutions were concentrated by ultrafiltration (Amicon) and stored at −70° C. The concentration of recombinant protein solutions were measured spectrophotometrically at 280 nm. An average extinction coefficient A of 1.6≅1 mg/ml was calculated from the amino acid composition of the six human α(IV)NC1 domains (20).

Recombinant α3(IV)NC1 expressed in kidney 293 cells and *E. coli* was prepared as described (21,22) Native human α3(IV)NC1 was isolated from glomerular basement membrane (23). Human kidneys unsuitable for transplantation were obtained from Midwest Organ Bank, Kansas City, Kans.

Sera.

The plasmapheresis fluid or sera from eight patients diagnosed with Goolpasture syndrome (GP1–8) were used. The titer of GP autoantibodies was measured by direct ELISA in plates (Nunc) coated with α3(IV)NC1 (100 ng/well). Relative to the GP1 serum previously described (24), GP 1–4 had about the same titer, GP 5–6 had a titer about 10-fold lower, and GP 7–8 had about 80-fold lower.

Western blots.

SDS-polyacrylamide gel electrophoresis (25) was performed in 4–20% gradient gels, under non-reducing conditions, using 500 ng protein per lane. For immunoblotting, the proteins (200 ng protein/lane) were transferred to nitrocellulose membranes, reacted with GP sera (1:100) and alkaline phosphatase-conjugated goat anti-human IgG (1:1000) then stained with 5-bromo-4-choro-3-indolyl phosphate and nitroblue tetrazolium.

Direct and inhibition immunoassays.

MaxiSorp™ polystyrene microtiter plates (Nunc, Denmark) were coated overnight at room temperatures with antigen (50–200 ng/well, as shown) in 50 mM carbonate buffer, pH 9.6, then blocked with casein or BSA. In some experiments, the antigen was reduced prior to coating by treatment with 10% β-mercaptoethanol for 5 at 100° C. GP sera and normal human sera (negative controls) were diluted in the incubation buffer (2% casein or 2 mg/ml BSA and 0.05% Tween 20 in TBS). Alkaline phosphatase-conjugated goat anti-human IgG (1:2000) was used as secondary antibody. p-Nitrophenol phosphate (1 mg/ml in 1 M diethanolamine buffer, pH 9.8, containing 0.5 mM zinc chloride) was used as substrate and the development of color was monitored at 410 nm in a Dynatech MR4000 plate reader. For inhibition ELISA, the GP sera were incubated overnight at room temperature with various amounts of recombinant α(IV)NC1 domains or chimeras prior to addition to plates coated with α3(IV)NC1. The results shown are the averages of duplicate determinations.

PEPSCAN analysis.

Mapping of linear epitopes was performed using the "PEPSCAN" method (26). A complete set of solid-phase overlapping 12-mer peptides was synthesized onto polyethylene pins following the published sequences of NC1 domains of α1(IV) (GenBank Accession Number P02462) and α3(IV) collagen (GenBank Accession Number X80031). The immunoscreening of these peptides was performed by ELISA. The pins were incubated for one hour with GP serum (diluted 1:50), then washed three times. The bound antibody was detected by the reaction with peroxidase-labeled secondary antibody for 30 minutes, followed by color development with 2,2'-azinobis-3-ethylbenzthiazolinesulfonic acid for another 30 minutes.

Results

Design and expression of α1/α3(IV)NCl chimeras.

In this study, α1/α3 chimeras were used to identify the conformational epitope(s) of the GP autoantigen. This strategy relied on the high sequence homology between the NCl domains of α1(IV) and α3(IV) collagen (71% sequence identity and six conserved disulfide bonds), which very likely adopt similar tertiary structures (27). In the chimeras, α1(IV)NCl acted as an inert "carrier" and provided a three-dimensional scaffold for the substituted α3(IV) sequences.

Since GP sera react preferentially with α3(IV)NCl, but not the other α(IV)NC1 domains, the autoepitope(s) must contain amino acids specific to α3(IV)NC1. Our recent comparative analysis of the sequences of α(IV)NC1 domains has now permitted the identification of six putative locations of the epitope(s) as short regions (less than 15 residues) in α3(IV)NC1 that are most divergent from other α(IV)NC1 domains and that are also predicted to be accessible to solvent (27). Accordingly, six chimeric NC1 domains (C1–C6) were constructed in which these α3(IV) NC1 sequences replaced the corresponding amino acids within the α1(IV)NC1 domain (FIG. 12). Five combination chimeras (C1•2, C1•4, C2•6, C3•5, C1•2•5) were also constructed to allow identification of non-contiguous GP epitopes.

To analyze two previously proposed GP epitopes (11,15, 28) using this approach, three additional chimeras (C7, C8 and C7•8) were constructed. The twenty-six N-terminal amino acids of C7 chimera, which included four collagenous Gly-X-Y triplets, were from the α3(IV) sequence. C8 contained the thirty-six C-terminal residues of α3(IV)NC1 and, in addition, had two α1(IV) Gly-X-Y triplets at the amino terminus. The additional Gly-X-Y sequences, also present in the native collagenase digested α1- and α3(IV)NC1 domains, were incorporated in the C7 and C8 chimeras to emulate the proteins previously used to amp the autoepitope (15).

Figure 13:
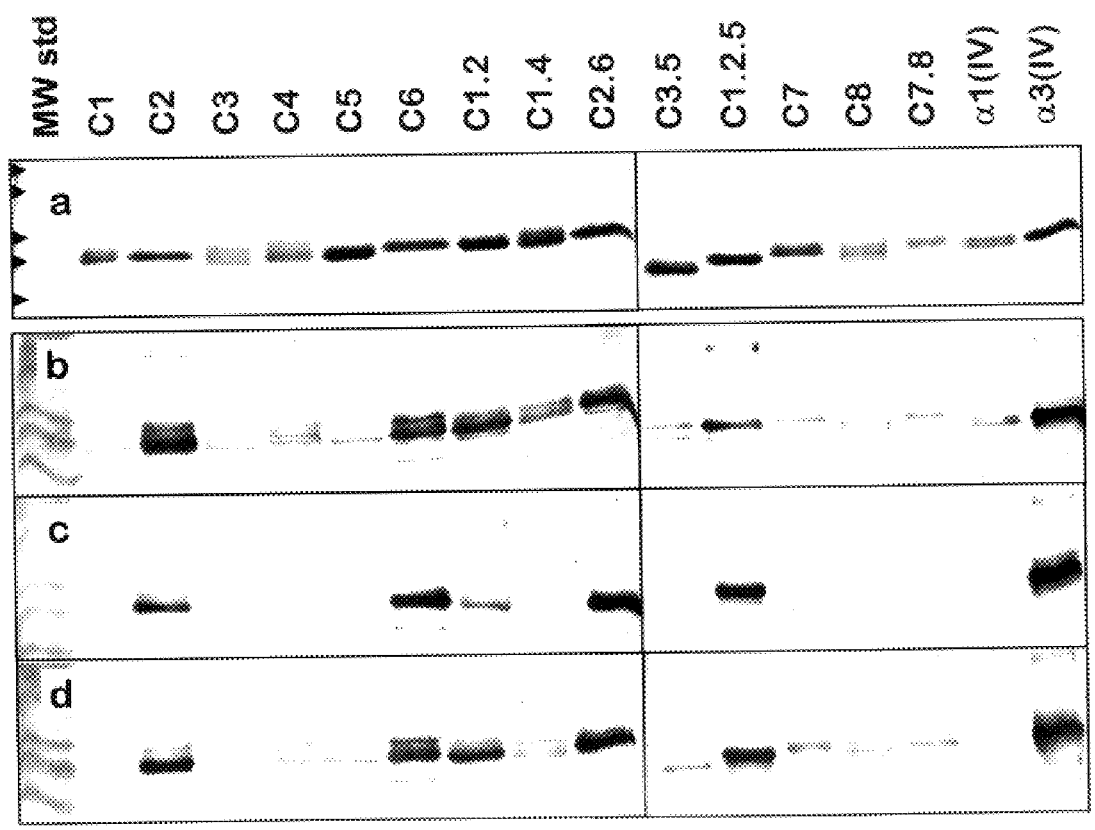

The recombinant chimeric proteins were expressed in the human embryonic kidney 293 cells and isolated from the culture medium as monomers with an apparent molecular weight of about 25–30 kDa by SDS-PAGE (FIG. 13a). Unlike expression in E. coli (22), expression in the human kidney 293 cells yields properly folded recombinant NC1 domains that are undistinguishable by FT-IR or immunoassays from those prepared from native sources[2]. This cell line has been successfully used to express other proteins with native folding, including basement membrane proteins nidogen (20) and laminin (30).

Immunoreactivity of α1/α3 chimeras with GP sera.

The reactivity of the chimeric constructs with GP sera was analyzed by Western blotting as well as by direct and inhibition ELISA assays. The pattern of autoantibody binding obtained in Western Blots with three sera show remarkable similarities (FIG. 13b–d). Only two chimeras, C2 and C6—containing residues 17–31 and 127–141 of α3(IV) NC1, respectively—reacted strongly and consistently with GP antibodies, as did combination chimeras containing one or both these regions (C1•, C2•6, C1•2•5). Some sera showed weak reactivity with other chimeras, but this appears to be due to the cross-reactivity with the α1 backbone, because it was accompanied by comparable binding to α1(IV)NC1. Remarkably, neither C7 nor C8 chimeras bound autoantibodies.

To confirm these findings, the binding of eight GP sera to immobilized chimeras was assessed in direct ELISA (FIG. 14). Sera were diluted proportionally to their titers to allow visualization of the specificity of the low-titer sera side by side with the high-titer sera. In general, the pattern of reactivity observed in the Western blots was also apparent in the ELISA. All sera reacted strongly with C2 chimeras (which averaged 71% of the maximal reactivity, obtained with α3(IV)NC1), C1•2 (47%) C2•6 (70%), and C1•2•5 (64%). There was more variation in the reactivity toward C6 chimera (31% of the reactivity of α3(IV)NC1), which bound significantly only five out of eight sera. All but one low-titer serum (GP-7) bound more to C2 than to C6 chimera. Sera that showed cross-reactivity with α1(IV)NC1 bound all chimeras, producing a higher background.

The relative reactivity of any given serum toward recombinant proteins was not influenced by the dilution of the serum. This was apparent in the titration curves shown in FIG. 15, which yielded parallel lines for various immobilized proteins. Similar results were obtained with the other sera. All sera had the highest reactivity toward α3(IV)NC1, which was closely followed by C2•6 and C2 chimeras (less than a two-fold difference in titers). The C6 chimera titers of the sera were more variable, between two- and ten-fold lower than the α3(IV)NC1 titers, but always higher than those of α1(IV)NC1 and α2(IV)NC1 controls.

Immunodominance of antibodies binding to C2 and C6 chimeras.

It is well established that adsorption of proteins to plastic may cause denaturation, so that the antibody binding measured in direct ELISA may actually be to the denatured antigen. To rule out such artifacts, the interaction between the GP antibodies and antigen was studied in solution by inhibition ELISA in the presence of soluble chimeras and control α(IV)NC1 domains. The inhibition curves were determined for three GP sera and were found to be similar. Typical data for one serum are shown in FIG. 16 (top panel). The inhibitory capacity of the chimeras and the control proteins followed the same order as found in direct ELISA, α3(IV)NC1>C2•>C2>C6>α1(IV)NC1, consistent with the results obtained with the latter technique. The effect of the chimeras was saturable, level off at the highest concentration used, where it produced 42–67% inhibition—a significant proportion of the autoantibody reactivity.

The α3(IV)NC1 domain could completely inhibit autoantibody binding and had an $I_{50}$ (the concentration of competitor at which half-maximal inhibition is achieved) of 0.27±0.03 μg/ml (about 11 nM), in good agreement with the previously reported values of 0.5 μg/ml (31) and 0.8 μg/ml (9). At high concentrations, α1(IV)NC1 but not α2(IV)NC1 inhibited autoantibody binding to α3(IV)NC1 by about 24%. This effect can be attributed to cross-reactivity, since α3(IV)NC1 is more similar to the α1- and α5(IV)NC1 domains than to α2-, α4- or α6(IV)(NC1 domains (27). An $I_{50}$ value could not be reliably calculated for chimeras because the inhibition curves they produced could not be fitted adequately to a simple inhibition model. Visual examination of these curves revealed a bi-phasic behavior. The steep inhibition below 2 μg/ml (FIG. 16, top panel) is probably due to the specific α3(IV) sequence in the chimeras, while the shallower portion of the curves at higher chimera concentrations, which parallels the α1(IV)NC1 inhibition curve, is likely caused by cross-reactivity with the α1(IV)NC1 scaffolding.

Figure 6:
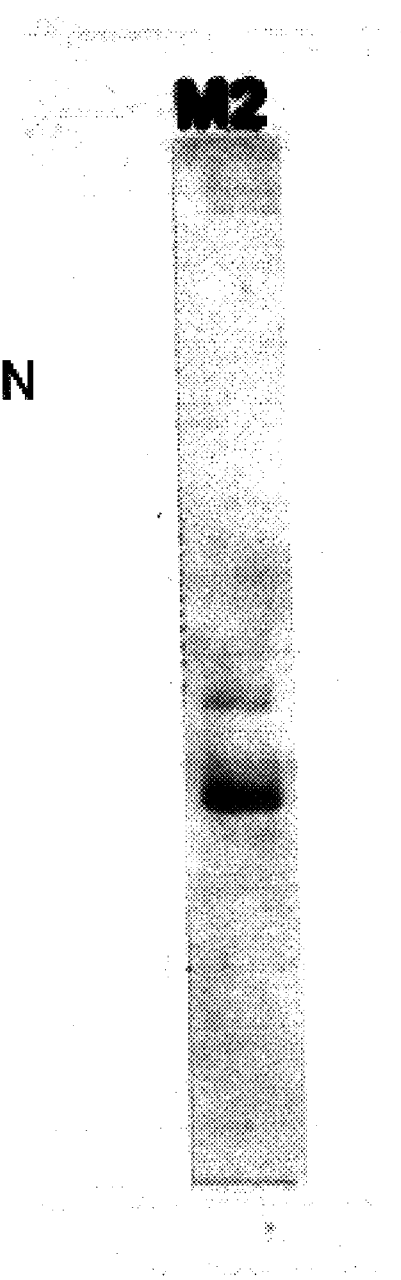

To quantitate the binding specificity of eight GP sera, an inhibition ELISA assay was performed at a fixed concentration of soluble antigen, 10 μg/ml (FIG. 6, bottom panel). This concentration was chosen to minimize cross-reactivity with α1(IV), while giving almost complete inhibition with α3(IV)NC1. Inhibition with C2•6 was 65%±13%, compared with 85%±7% for control α3(IV)NC1, demonstrating that this chimera contains the immunodominant autoepitope(s) of α3(IV)NC1. C2•6 chimera had a stronger effect than either C2 (46%±8%) or C6 chimeras (23%±18%). This indicates that the α3(IV)NC1 residues 17–31 (hereafter referred to as $E_A$) and 127–141 (hereafter referred to as $E_B$) form either two separate epitopes or a single, more complete one, but it appears to rule out significant cross-reactivity between the two homologous sequences.

The data were further analyzed to estimate the fraction of autoreactivity that could be attributed specifically to the α3(IV)NC1 sequences in the chimeras. For each serum, the inhibition produced by the α1(IV)NC1 domain (which averaged 7%±4%) was subtracted from the total inhibition given by the chimeras to correct for the cross-reactivity due to the common scaffold, then the results were normalized to the effect produced by α3(IV)NC1 (FIG. 17). The effect of $E_A$ (present in C2 chimera) was strong and consistent (on average 47%, ranging between 27–64%), and predominated in seven out of eight sera. In contrast, $E_B$ (present in C6 chimera) produced variable inhibition with different sera (on average 18%, ranging between 3–56%) and was predominant only in GP-7. Together, as in C2•6 chimera, these sequences accounted for most inhibition of PG sera (on average 68%, ranging between 52–88%). Only a small fraction of GP reactivity toward α3(IV)NC1 (on average 23%, ranging between 6–38%) could not be accounted for by $E_A$, $E_B$, or by cross-reactivity with α1(IV)NC1.

Conformational nature of the epitope(s).

Figure 18:
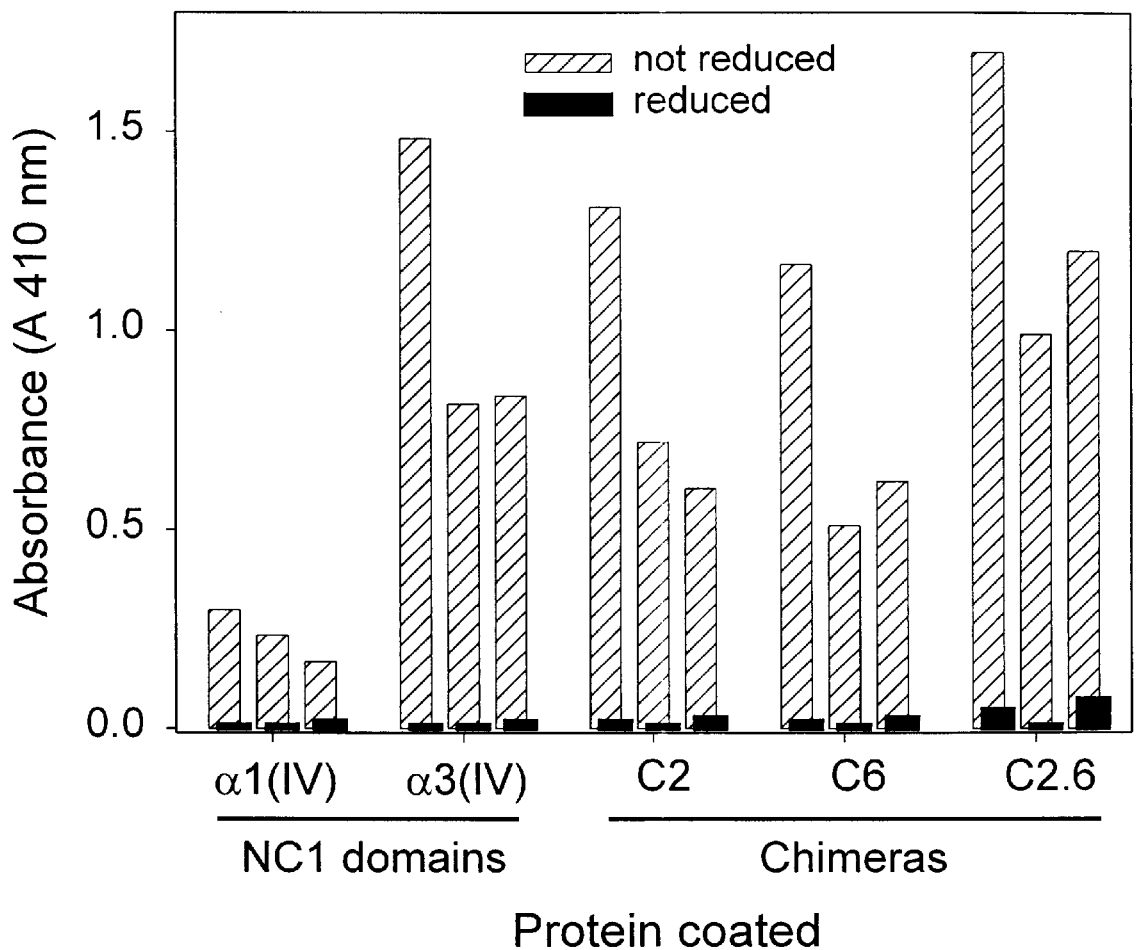

It has been previously shown that the reduction of disulfide bonds in α3(IV)NC1 impairs its ability to react with GP antibodies, indicative of a conformational epitope (9–11). Quantitation of this effect with the eight sera used in the present word showed that only 6%±5% of the original immunoreactivity remains after reduction of α3(IV)NC1. To evaluate whether $E_A$ and $E_B$ form a linear or a conformational epitope, the GP reactivity of the α1/α3 chimeras was measured before and after reduction. As in α3(IV)NC1, the reduction of disulfide bonds also abolished binding of autoantibodies to the C2, C6 and C2•6 chimeras, and even to α1(IV)NC1 (FIG. 18). Less than 10% of the original immunoreactivity remained in the reduced proteins, although they had the same or higher reactivity with monoclonal antibodies that do not require a conformational epitope, such as anti-FLAG (data not shown). Overall, these results demonstrate that only a small proportion of the GP antibodies can recognize linear epitopes, and that $E_A$ and $E_B$ belong to one or two conformational GP epitopes that are disulfide-bond-dependent.

Comparison of chimera-based epitope mapping with previous approaches.

Figure 19:
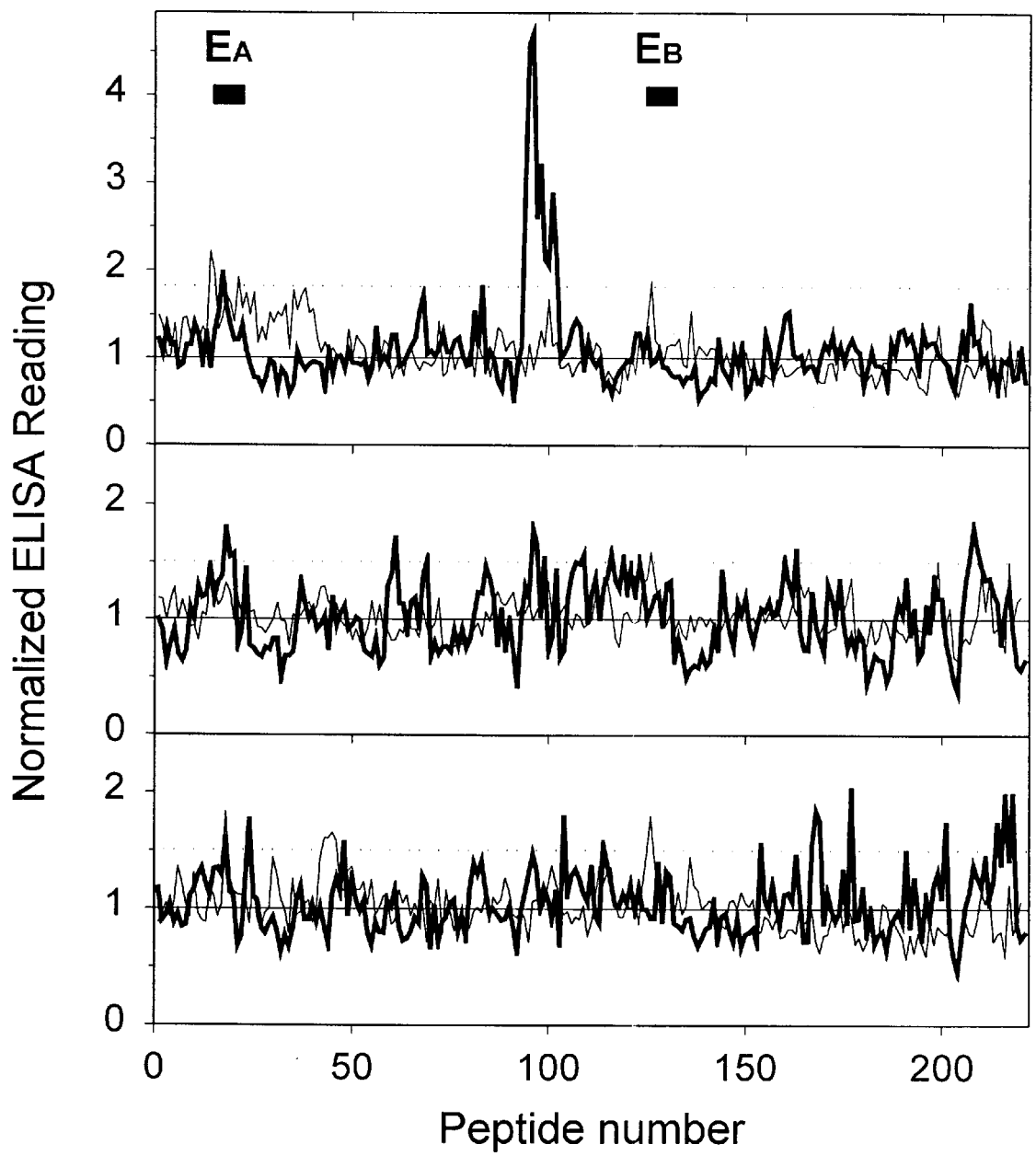

To compare the chimera-based epitope mapping strategy with approaches using linear peptides (9,11,13,14) and to evaluate whether the latter identify linear or conformational GP epitopes, a peptide scanning analysis was performed. A valid comparison between the chimera-based and peptide-based strategies required using the same GP sera. Two complete sets of overlapping 12-mers based on the α1(IV)- and α3(IV)NC1 sequences (FIG. 19) were therefore synthesized and analyzed by the PEPSCAN procedure (26). A previous report using 20-mer peptides to map the GP epitope has indicated non-specific binding of GP sera to homologous α1- and α3-IV)NC1 peptides (9).

The PEPSCAN results demonstrated lack of strong specific binding and a high background, presumably due to non-specific binding. Both α1- and α3(IV)NC1 sequences produced a number of peaks higher than two standard deviations above the median. However, the most reactive peptides (above three standard deviations) varied among the three GP sera tested. The most significant PEPSCAN peak was produced by peptides overlapping residues 94–110 of α3(IV)NC1 with the GP-2 serum. Much weaker reactivity was recorded in this region with the other two sera. This region corresponds to the C5 chimera that did not interact with GP sera in direct ELISA (FIG. 14), perhaps due the conformations of the 12-mer peptides on the pin being different from those adopted by the same amino acids in the NC1 domain. Some isolated α3-derived peptides that overlapped the $E_A$ region produced peaks in PEPSCAN. However, the interactions were not strong enough to allow unambiguous identification of these residues as part of a GP autoepitope.

Figure 20:
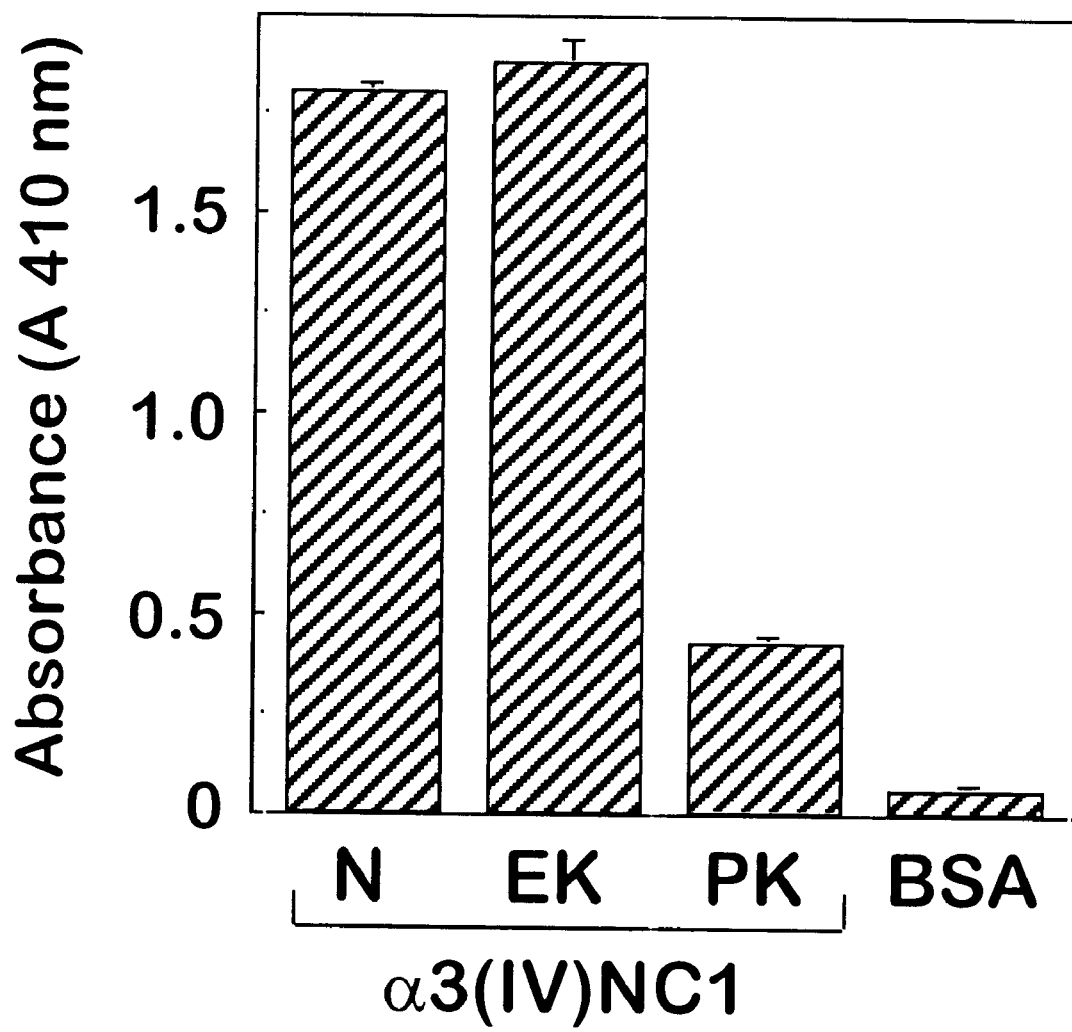

Two epitopes previously found by mutagenesis of α3(IV) NC1 expressed in *E. coli* (15) were not observed in C7 and C8 chimeras, made in eukaryotic cells in the present work. Recombinant α3(IV)NC1 expressed in *E. coli* was found about four times less reactive than the native human protein (FIG. 20), in agreement with earlier reports (22). In contrast, the recombinant α3(IV)NC1 used in this work, expressed in 293 kidney cells, was found as reactive as native human α3(IV)NC1 (FIG. 20). This suggests a folding difference whereby the full complement of conformational epitopes is not assembled in the *E. coli*-made protein. It is also possible that mutagenesis to alanine of residues from *E. coli* α3(IV) NC1 may have caused the reported loss of GP immunoreactivity by affecting the overall structure of the protein and not the epitope itself.

Discussion

In the present study, a new strategy based on chimeric proteins was employed to map regions within α3(IV)NC1 that constitute the conformational epitope(s) for GP autoantibodies. This novel approach has two methodological improvements over previous work. Unlike in peptide-based epitope mapping, short α3(IV)NC1 candidate regions (<15 residues) were grafted onto an inert α1(IV)NC1 framework and expressed in mammalian cells to ensure native folding. The resulting chimeras were assayed for "gain-of-function", i.e. capacity to bind autoantibodies, in contract with previous site-directed mutagenesis studies (15) that relied on a "loss-of-function" of the protein expressed in *E. coli*. The results from fourteen different chimeras revealed two previously unidentified regions, designated $E_A$ and $E_B$ (residues 17–31 and 127–141 of α3(IV)NC1, respectively),that strongly bound autoantibodies from eight GP patients. Together, $E_A$ and $E_B$ accounted for 50–90% (on average 68%) o auto-reactivity to α3(IV)NC1.

Among the six candidate regions evaluated in this study, regions $E_A$ and $E_B$ clearly exhibited a distinct capacity to bind GP antibodies by Western Blots, direct ELISA, and inhibition ELISA. The six regions were selected based on the following: a) autoantibodies preferentially bind the α3(IV)NC1 domain, but not the other five homologous NC1 domains of type IV collagen; b) therefore, regions of substantial sequence divergence between α3(IV)NC1 and the other NC1 domains confer antibody binding to the former. The four regions that were found non-reactive (i.e., those substituted in C1, C3, C4 and C5 chimeras) further distinguish $E_A$ and $E_B$ as the primary regions for the GP epitope. It is significant that the $E_A$ and $E_B$ regions are homologous (47% sequence identity) and are located at corresponding positions in the two homologous NC1 subdomains (27), but they are noncontiguous. $E_A$ and $E_B$ could represent two separate and distinct epitopes or a single epitope $E_{AB}$, in which $E_A$ and $E_B$ are held in close proximity to each other by the disulfide bonds. In either case, the complete epitope (s) probably includes additional residues from other regions, less critical for binding. So far, the X-ray crystallographic structures of other protein-antibody complexes have revealed noncontiguous epitopes of 15–22 amino acids that belong to several surface loops (32,33).

Our results demonstrate that regions $E_A$ and $E_B$ reproduce very well the authentic GP epitopes in the α3(IV)NC1 domain. Most remarkably, $E_A$ and $E_B$ form conformational epitopes that require intact disulfide bonds to bind GP antibodies, as demonstrated by loss of GP immunoreactivity of the C2, C6 and C2•6 chimeras upon reduction (FIG. 16). The majority of GP autoantibodies appears to recognize conformational epitopes in α3(IV)NC1 (9–11), but epitope mapping studies have not addressed until now the nature of the epitopes found (vide infra). Further demonstrating the good mimicry of the original epitope(s), the chimeras produced significant inhibition of GP sera at concentrations in the range of $10^{-8}$ M, comparable with α3(IV)NC1 domain. In contrast, linear α3(IV)NC1 peptides produced a comparable effect in inhibition ELISA only at concentrations 100–1000-fold higher (11,14).

The $E_A$ and $E_B$ regions have not been previous identified by peptide-based epitope mapping (9,11–14). As shown here, this was due to the inability of peptide scanning procedures to reliably identify the conformational GP epitope(s). An intrinsic tendency of peptide-based methods to identify sequential epitopes has already been noted (34). Thus, the α1(IV)NC1 framework of the chimeras is instrumental for adoption of the native conformation by $E_A$ and $E_B$, and, in addition, it may contributed auxiliary residues for binding. It is likely that the previous reports have largely identified linear GP epitopes, which constitute a minority (about 5% of the reactivity against α3(IV)NC1). Furthermore, various linear sequences were found reactive in different studies, suggesting heterogeneity of the linear epitopes. In contrast, the chimera-based approach has successfully identified the critical regions of one or two immunodominant, conformational GP epitope(s) that were consistently recognized by all autoimmune sera used in this work.

Region $E_A$ clearly represents an immunodominant epitope. It was recognized strongly and consistently by all sera analyzed, whereas $E_B$ reacted significantly (>10%) with only half of the sera. This may be due to the higher divergence of $E_A$ (eight distinct amino acids) compared with $E_B$ (five distinct amino acids). The existence of an immunodominant epitope explains the considerable cross-inhibition between GP sera from different patients or between GP sera and certain monoclonal antibodies (13,31, 35). $E_A$ and $E_B$ may well be the counterpart of the shared structural determinants on the GP antibodies, found by using an anti-idiotype antibody against anti-α3(IV) IgG (36).

In summary, two specific homologous sequences in α3(IV)NC1 have been identified for the first time to be parts of one or two disulfide bond-dependent, conformational and immunodominant GP autoepitopes. This finding provides new knowledge to further investigate the pathogenesis of GP disease. It has recently been shown that α3(IV)NC1 but not α1(IV(NC1 can induce experimental GP disease in mice (21). A very important question, relevant for the identification of the nephritogenic epitope(s) in α3(IV)NC1, is whether any of the α1/α3 chimeras can induce experimental GP syndrome. In myasthenia gravis, another autoimmune disease, the immunodominant epitope on the acetylcholine receptor (known as "MIR", or main immunogenic region) was also pathogenic (37). By providing a highly specific target, the new identification of an immunodominant GP epitope should be useful for the development of more specific therapeutic approaches, such as use of vaccines to induce tolerance or the manipulation of the idiotype network.

References for Example 19

1. Wilson, C., and Dixon, F. (1986) in *The Kidney* (Berner, B., and Rector, F., eds), 3rd Ed., pp. 800–889, Saunders, Philadelphia 2. Hudson, B. G., Reeders, S. T., and Tryggvason, K., (1993) *J. Biol. Chem.* 268, 26033–26036

3. Gunwar, S., Ballester, F., Noelken, M. E., Sado, Y., Ninomiya, Y.,and Hudson, B. G. (1988) *J. Biol. Chem.* 273, 8767–8775

4. Mariyama, M., Leinonen, A., Mochizuki, T., Tryggvason, K., and Reeders, S. T. (1994) *J. Boil. Chem.* 269, 2313–23017

5. Butkowski, R. J., Langeveled, J. P., Wieslander, J., Hamilton, J., and Hudson, B. G. (1987) *J. Biol. Chem.* 262, 7874–7877

6. Saus, J., Wieslander, J., Langeveld, J. P., Quinones, S., and Hudson, B. G. (1988) *J. Biol. Chem.* 263, 13374–13380

7. Kalluri, R., Wilson, C. B., Weher, M., Gunwar, S., Chonko, A. M., Neilson, E. G., and Hudson, B. G. (1995) *J. Am. Soc. Nephrol.* 6, 1178–1185

8. Dehan, P., Weber, M., Zhang, X., Reeders, S. T., Foidart, J. M., and Tryggvason, K. (1996) *Nephrol. Dial. Transplant.* 11, 2215–2222

9. Hellmark, T., Brunmark, C., Trojnar, J., and Wieslander, J. (1996) *Clin. Exp. Immunol.* 105, 504–510

10. Wieslander, J., Bygren, P., and Heinegard, D. (1984) *Proc. Natl. Acad. Sci. USA* 81, 1544–1548

11. Kalluri, R., Gunwar, S., Reeders, S. T., Morrison, K. C., Mariyama, M., Ebner, K. E., Noelken, M. E., and Hudson, G. B. (1991) *J. Biol. Chem.* 266, 24018–24024

12. Kefalides, N. A., Ohno. N., Wilson, C. B., Fillit, H. Zabriski, J., and Rosenbloom, J. (1993) *Kidney Int.* 43, 94–100

13. Levy, J. B., Turner, A. N., George, A. J., and Pusey, C. D. (1996) *Clin. Esp. Immunol.* 106, 79–85

14. Levy, J. B., Coulthart, A., and Pusey, C. D. (1997) *J. Am. Soc. Nephrol.* 8, 1698–1705

15. Kalluri, R., Sun, J. J., Hudson, B. G., and Neilson, E. G. (1996) *J. Biol. Chem.* 271, 9062–9068

16. Hsia, R., Beals, T., and Boothroyd, J. C. (1996) *Mol. Microbiol.* 19, 53–63

17. Henriksson, E. W., and Pettersson, I. (1997) *J. Autoimmun.* 10, 559–568

18. Mayer, U., Poschl, E., Nischt, R., Specks, U., Pan. T. C., Chu, M. L., and Timpl, R. (1994) *Eur. J. Biochem.* 225, 573–580

19. Sambrook, J. (1989) in *Molecular Cloning: a laboratory manual* (Fritsch, E. F., and Maniatis, T., eds) Vol. 3, 2nd Ed., pp. 16.32, Cold Spring Harbor Lab. Press, U.S.A.

20. Gill, S. C., and von Hippel, P. H. (1989) *Anal. Biochem.* 182, 319–326

21. Sado, Y., Boutaud, A., Kagawa, M., Naito. I., Ninomiya, Y., and Hudson, B. G. (1998) *Kidney Int.* 53, 664–671

22. Neilson, E. G., Kalluri, R., Sun, M. J., Gunwar, S., Danoff, T., Mariyama, M., Myers, J. C., Reeders, S. T., and Hudson, B. G. (1993) *J. Biol. Chem.* 268, 8402–8405

23. Wieslander, J., Kataja, M., and Hudson, B. G. (1987) *Clin. Esp. Immunol.* 69, 332–340

24. Gunwar, S., Ballester, F., Kalluri, R., Timoneda, J., Chonko, A. M., Edwards, S. J., Noelken, M. E., and Hudson, B. G. (1991) *J. Biol. Chem.* 266, 15318–15324

25. Laemmli, U. K. (1970) *Nature (London)* 227, 680–685

26. Geysen, H. M., Meloen, R. H., and Barteling, S. J. (1984) *Proc. Natl. Acad. Sci. USA* 81, 3998–4002

27. Netzer, K., Suzuki, K., Itoh, Y., Hudson, B. G., and Khalifah, R. G. (1998) *Protein Sci.* 7, 1340–1351

28. Penades, J. R., Bernal, D., Revert, F., Johansson, C., Frequent, V. J. Cervers, J., Wieslander, J., Quinones, S., and Saus, J. (1995) *Eur. J. Biochem.* 229, 754–760

29. Fox., J. W., Mayer, U., Nischt, R., Aumailley, M., Reinhardt, D., Wiedemann, H., Mann, K., Timpl, R., Krieg, T., Engel, J., and et al. (1991) *EMBO J.* 10, 3137–3146

30. Yurchenco, P. D., Quan, Y., Colognato, H., Mathus, T., Harrison, D., Yamada, Y., and O'Rear, J. J. (1997) *Proc. Natl. Acad. Sci. USA* 94, 10189–10194

31. Hellmark, T., Johansson, C., and Wieslander, J. (1994) *Kidney Int.* 46, 823–839

32. Laver, W. G., Air, G. M., Webster, R. G., and Smith-Gill, S. J. (1990) *Cell* 61, 553 . 556

33. Jones, S., and Thornton, J. M. (1996) *Proc. Natl. Acad. Sci. USA* 93, 13–20

34. Schwab, C., Twardek, A., Lo, T. P., Brayer, G. D., and Bosshard, H. R. (1993) *Protein Sci.* 2, 1975–182

35. Pusey, C. D., Dash, A., Kershaw, M. J., Morgan, A., Reilly, A., Rees, A. J., and Lockwood, C. M. (1987) *Lab. Invest.* 56, 23–31

36. Meyers, K. E., Kinniry, P. A., Kalluri, R., Neilson, E. G., and Madaio, M. P. (1998) *Kidney Int.* 53, 402–407

37. Tzartos, S. J., Cung, M. T., Demange, P., Lourtrari, H., Mamalaki, A., Marraud, M., Papdouli, L. Sakarellos, C., and Tsikaris, V. (1991) *Mol. Neurobiol.* 5, 1–29

References

1. Timpl, R., Wiedermann, H., Van Delden, V., Furthmayr, H., and Kuhn, K. (1981) *Eur. J. Biochem.* 120, 203–211
2. Martin, G. R., Timpi, R., and Kuhn, K. (1988) *Adv. Protein Chem.* 39, 1–50
3. Timpi, R., (1989) *Eur. J. Biochem.* 180, 487–502
4. Hostikka, S. L., and Tryggvason, K. (1988) *J. Biol. Chem.* 283, 19488–19493
5. Soininen, R., Haka-Risku, T., Prockop, D. J., and Tryggvason, K. (1987) *FEBS Lett.* 225, 188–194
6. Muthukumaran, G., Blumberg, B., and Kurkinen, M. (1989) *J. Biol. Chem.* 264, 6310–6317
7. Saus, J., Quinones, S., Mackrell, A., Blumberg, B., Muthukumaran, G., Pihlajaniemi, T., and Kurkiven, M. (1989) *J. Biol. Chem.* 264, 6318–6324.
8. Blumberg, B., MacKrell, A. J., and Fessier, J. H. (1988) *J. Biol. Chem.* 263, 18328–18337
9. Butkowski, R. J., Wieslander, J., Wisdom, B. J., Barr, J. F., Noelkan, M. E., and Hudson, B. G. (1985) *J. Biol. Chem.* 260, 3729–3747
10. Wieslander, J., Langeveld, J., Butkowski, R., Jodlowski, M., Noelken, M., and Hudson, B. G. (1985) *J. Biol. Chem.*, 260, 8564–8570
11. Butkowski, R., Langeveld, J. P. M., Wieslander, J., Hamilton, J., and Hudson, B. G. (1987) *J. Biol. Chem.* 262, 7874–7877
12. Butkowski, R., Shen, G-Q., Wieslander, J., Michael, A. F., and Fish, A. J. (1980) *J. Lab. Clin. Med.* 115, 365–373
13. Saus, J., Wieslander, J., Langeveld, J. P. M., Quinones, S., and Hudson, B. G. (1988) *J. Biol. Chem.* 263, 13374–13380
14. Hudson, B. G., Wieslander, J., Wisdon, B. J. Jr., and Noelken, M. G. (1989) *Lab. Invest.* 61, 256–269
15. Kieppel, M. M., Michael, A. F. and Fish, A. J. (1986) *J. Biol. Chem.* 261, 16547–16552
16. Jeraj, K., Kim, Y., Vernier, R. L., Fish, A. J., and Michael, A. F. (1983) *Am. J. Kidney Dis II*, 626–629
17. Kashtan, C., Fish, A. J., Kieppel, M., Yoshioka, K., and Michael, A. F. (1986) *J. Clin. Invest.* 78, 1035–1044
18. Kleppel, M. M., Kashtan, C. E., Butkowski, R. J., Fish, A. J., and Michael, A. F., (1987) *J. Clin. Invest.* 80, 263–266
19. Jenis, E. H., Valeski, J. E., Calcagno, P. L. (1981) *Clin. Nephrol.* 15, 111–114.
20. Olson, D. L., Anand, S. K., Landing B. H., Heuser, E., Grushkin, C. M., and Lieberman, E. (1980) *J. Peiatr.* 96, 697–699
21. Savage. C. O. S., Pusey, C. D., Kershaw, M. J., Cashman, S. J., Harrison, P., Hartley, B., Turner, D. R., Cameron, J. S., Evans, D. J., and Lockwood, C. M. (1986) *Kidney Int.* 30, 107–112
22. Hostikka, S. L., Eddy, R. L., Byers, M. G., Hoyhtya, M. Shows, T. B., and Tryggvason, K., (1990) *Proc. Natl. Acad. Sci. U.S.A.* 87, 1606–1610
23. Myers, J. C., Jones, T. A., Pohjolainen, E-R., Kadri, A. S., Goddard, A. D., Sheer, D., Solomon, E., and Pihlajaniemi, T. (1990) *Am. J. Hum. Genet.* 46, 1024–1033
24. Atkin, C. L., Hasstedt, S., Menlove, L., Cannon, L., Kirschner, N., Schwartz, C., Nguyenk, K. and Skoinck, M. (1988) *Am. J. Humn. Genet.* 42, 249–255
25. Brunner, H., Schroder, C., van Bennekom, C., Lambermon, E., Tuerlings, J., Menzel, D., Oining, H., Monnens, L., Wieringa, B. and Ropers, H.-H. (1988) *Kidney Inc.* 34, 507–510
26. Szpiro-Tapia, S., Bobrie, G., Guilloud-Bataille, M., Heuertz. S., Julier, C., Frezal, J., Grunfeld, J. P. and Hors-Cayla, M. C. (1988) *Hum. Genet.* 81, 85–87
27. Flinter, F. A., Abbs, S., and Bobrow, M. (1988) *Genomics* 4, 335–338
28. Barker, D. F., Hostikka, S. L., Zhou, J., Chow, L. T., Oliphant, A. R., Gerken, S. C., Gregory, M. C., Skilnick, M. H., Atkin, C. L., and Tryggvason, K. (1990) *Science* 248, 1224–1227
29. Pihiajaniemi, T., Tryggvason, K., Myers, J. C., Kurkinen, M., Lebo, R., Cheung, M-C., Prockop, D. J., and Boyd, C. D. (1985) *J. Biol. Chem.* 260, 7681–7687
30. Gunwar, S., Saus, J., Noelken, M. E., and Hudson, G. G. (1990) *J. Boil, Chem.* 265, 5466–5469
31. Grunfeld, J-P. (1985) *Kidney Int.* 27, 83–92
32. Hinglais, N., Grunfled, J-P., Bois, E. (1972) *Lab. Invest.* 27, 473–487
33. Yoshikawa, N., Cameron, A. H., White, R. H. R. (1981) *J. Pathol.* 135, 199–209
38. Ryan., J. J., Mason, P. J., Pusey, C. D., and Turner, N. (1988) *Clin. Exp. Immunol.* 113, 17–27

I claim:

1. A method of detecting Goodpasture antibodies from a bodily fluid or tissue from a patient comprising contacting the bodily fluid or tissue with an α(IV)NC1 polypeptide that contains a conformational epitope for the Goodpasture antibodies, wherein the conformational epitope comprises at least one amino acid sequence selected from the group consisting of TAIPSCPEGTVPLYS (SEQ ID NO. I) and TDIPPCPHGWISLWK (SEQ ID NO. II).

2. The method of claim 1, wherein the peptide is labeled with a detectable label and wherein the detection of the antibodies comprises detecting the label on the peptide.

3. The method of claim 1 wherein an ELISA is employed for detecting the presence of Goodpasture antibodies.

4. The method of claim 1 wherein the bodily fluid is selected from the group consisting of whole blood, blood plasma, and serum from a human patient.

5. A method of treating Goodpasture syndrome in a patient by neutralizing Goodpasture antibodies in the patient's blood or liquid fraction thereof by contacting the blood or liquid fraction thereof with an effective antibody neutralizing amount of an α(IV)NC1 polypeptide that contains a conformational epitope for Goodpasture antibodies, wherein the conformational epitope comprises, at least one amino acid sequence selected from the group consisting of TAIPSCPEGTVPLYS (SEQ ID NO. I) and TDIPPCPHG-WISLWK (SEQ ID NO. II).

6. The method of claim 5 wherein the polypeptide is bound to a solid support, wherein the blood or liquid fraction thereof is withdrawn from the patient, wherein the withdrawn blood or liquid fraction thereof is passed over the polypeptide to remove the Goodpasture antibodies, and wherein the blood or liquid fraction thereof is then returned to the blood stream of the patient.

7. The method of claim 6 wherein the liquid fraction of blood is blood plasma and the patient is human.

* * * * *

SEQUENCE LISTING

<160> NUMBER OF SEQ ID NOS: 65

<210> SEQ ID NO: 1
<211> LENGTH: 1416
<212> TYPE: DNA
<213> ORGANISM: Bos taurus
<220> FEATURE:
<221> NAME/KEY: CDS
<222> LOCATION: (1)..(1416)

<400> SEQUENCE: 1

```
ggc ctc cct ggc agg aaa ggg cca gtg gga gat gct ggg cct cca ggc      48
Gly Leu Pro Gly Arg Lys Gly Pro Val Gly Asp Ala Gly Pro Pro Gly
  1               5                  10                  15 cag ctt ggc gtg aca gga cct caa ggg gca cca ggc ttt cct ggt gta      96
Gln Leu Gly Val Thr Gly Pro Gln Gly Ala Pro Gly Phe Pro Gly Val
```

-continued

```
                    20                      25                      30
acc atc cct ggc cag aaa gga gat cga ggt cca cct ggc tcc aga gga        144
Thr Ile Pro Gly Gln Lys Gly Asp Arg Gly Pro Pro Gly Ser Arg Gly
            35                      40                      45 aac cca ggc atg cct ggt cct cct gga cct cca ggg agt cct gta gaa        192
Asn Pro Gly Met Pro Gly Pro Pro Gly Pro Pro Gly Ser Pro Val Glu
    50                      55                      60 ggc ata aaa gga gac aag ggg ttg atg gga gag cct ggc caa aga ggt        240
Gly Ile Lys Gly Asp Lys Gly Leu Met Gly Glu Pro Gly Gln Arg Gly
65                      70                      75                      80 cca cct gga gct ata gga gac atg ggg tca cca ggt cat ccg gga gca        288
Pro Pro Gly Ala Ile Gly Asp Met Gly Ser Pro Gly His Pro Gly Ala
                        85                      90                      95 cca ggt gtc ccc ggt cag cca ggg gcc aga ggt gat cct gga ttc tat        336
Pro Gly Val Pro Gly Gln Pro Gly Ala Arg Gly Asp Pro Gly Phe Tyr
            100                     105                     110 gga ttt cca ggc atg aaa ggg aag aag ggt aat tca gga ttt cca gga        384
Gly Phe Pro Gly Met Lys Gly Lys Lys Gly Asn Ser Gly Phe Pro Gly
    115                     120                     125 cca cct gga cct cca ggg caa agt gga cca aaa gga cca cct gga gta        432
Pro Pro Gly Pro Pro Gly Gln Ser Gly Pro Lys Gly Pro Pro Gly Val
130                     135                     140 cgt gga gag cct ggc aca gtg aag atc atc tcc ctt cca gga agc cca        480
Arg Gly Glu Pro Gly Thr Val Lys Ile Ile Ser Leu Pro Gly Ser Pro
145                     150                     155                     160 ggc cca cct ggt tca gct gga gaa cca ggg atg caa gga gaa ccc ggg        528
Gly Pro Pro Gly Ser Ala Gly Glu Pro Gly Met Gln Gly Glu Pro Gly
                        165                     170                     175 ccc cca gga cca cca gga gat cca gga ccc tgt ggg cca aaa ggt aaa        576
Pro Pro Gly Pro Pro Gly Asp Pro Gly Pro Cys Gly Pro Lys Gly Lys
            180                     185                     190 cca ggg gag gat ggt cca cca gga act cct gga cca act gga gaa aaa        624
Pro Gly Glu Asp Gly Pro Pro Gly Thr Pro Gly Pro Thr Gly Glu Lys
    195                     200                     205 ggc aac aaa ggt tgt aaa gga gag caa gga cca cct gga tcc gat ggc        672
Gly Asn Lys Gly Cys Lys Gly Glu Gln Gly Pro Pro Gly Ser Asp Gly
210                     215                     220 ctg cca ggc ttg aag ggg aaa cct gga gac act gga cca cct gca gca        720
Leu Pro Gly Leu Lys Gly Lys Pro Gly Asp Thr Gly Pro Pro Ala Ala
225                     230                     235                     240 ggg gca gtg atg agg ggc ttt gtc ttt acc cgg cac agc cag acc aca        768
Gly Ala Val Met Arg Gly Phe Val Phe Thr Arg His Ser Gln Thr Thr
                        245                     250                     255 gca att ccc tcc tgt cca gaa ggg aca gag ccg ctc tat agt ggg ttt        816
Ala Ile Pro Ser Cys Pro Glu Gly Thr Glu Pro Leu Tyr Ser Gly Phe
            260                     265                     270 tct ctt ctc ttt gta caa gga aat gaa caa gcc cat gga cag gac ctg        864
Ser Leu Leu Phe Val Gln Gly Asn Glu Gln Ala His Gly Gln Asp Leu
    275                     280                     285 gga aca ctt ggc agc tgc ctg cag cga ttt acc aca atg cca ttc tta        912
Gly Thr Leu Gly Ser Cys Leu Gln Arg Phe Thr Thr Met Pro Phe Leu
290                     295                     300 ttc tgc aat atc aac gat gta tgt aat ttt gca tct cga aac gat tat        960
Phe Cys Asn Ile Asn Asp Val Cys Asn Phe Ala Ser Arg Asn Asp Tyr
305                     310                     315                     320 tca tac tgg ctg tca aca cca gct atg ata cca atg gac atg gct cca       1008
Ser Tyr Trp Leu Ser Thr Pro Ala Met Ile Pro Met Asp Met Ala Pro
                        325                     330                     335 att act ggc agg gcc ctg gag cct tat att agc aga tgt aca gtc tgt       1056
```

-continued

```
Ile Thr Gly Arg Ala Leu Glu Pro Tyr Ile Ser Arg Cys Thr Val Cys
        340                 345                 350 gaa ggt cct gca att gcc ata gct gtt cac agc caa acc act gat atc    1104
Glu Gly Pro Ala Ile Ala Ile Ala Val His Ser Gln Thr Thr Asp Ile
355                 360                 365 ccc ccc tgt cct gct ggc tgg att tct ctc tgg aaa ggc ttt tct ttc    1152
Pro Pro Cys Pro Ala Gly Trp Ile Ser Leu Trp Lys Gly Phe Ser Phe
    370                 375                 380 atc atg ttc aca agt gct ggt tcg gag ggt gct ggg caa gca ctc gca    1200
Ile Met Phe Thr Ser Ala Gly Ser Glu Gly Ala Gly Gln Ala Leu Ala
385                 390                 395                 400 tcc ccc ggc tcc tgc ctg gaa gaa ttc cga gcc agt cca ttt ata gaa    1248
Ser Pro Gly Ser Cys Leu Glu Glu Phe Arg Ala Ser Pro Phe Ile Glu
                405                 410                 415 tgt cac gga aga gga aca tgt aac tac tat tca aac tcc tac agt ttc    1296
Cys His Gly Arg Gly Thr Cys Asn Tyr Tyr Ser Asn Ser Tyr Ser Phe
            420                 425                 430 tgg ttg gct tca tta gac ccc aaa aga atg ttc aga aaa cct att cca    1344
Trp Leu Ala Ser Leu Asp Pro Lys Arg Met Phe Arg Lys Pro Ile Pro
        435                 440                 445 tca act gtg aaa gct ggg gag tta gaa aac ata ata agt cgc tgt caa    1392
Ser Thr Val Lys Ala Gly Glu Leu Glu Asn Ile Ile Ser Arg Cys Gln
450                 455                 460 gtg tgc atg aag atg aga cca tga                                    1416
Val Cys Met Lys Met Arg Pro
465                 47
```

<210> SEQ ID NO: 2
<211> LENGTH: 471
<212> TYPE: PRT
<213> ORGANISM: Bos taurus

<400> SEQUENCE: 2

```
Gly Leu Pro Gly Arg Lys Gly Pro Val Gly Asp Ala Gly Pro Pro Gly
  1               5                  10                  15

Gln Leu Gly Val Thr Gly Pro Gln Gly Ala Pro Gly Phe Pro Gly Val
                 20                  25                  30

Thr Ile Pro Gly Gln Lys Gly Asp Arg Gly Pro Pro Gly Ser Arg Gly
             35                  40                  45

Asn Pro Gly Met Pro Gly Pro Pro Gly Pro Pro Gly Ser Pro Val Glu
         50                  55                  60

Gly Ile Lys Gly Asp Lys Gly Leu Met Gly Glu Pro Gly Gln Arg Gly
 65                  70                  75                  80

Pro Pro Gly Ala Ile Gly Asp Met Gly Ser Pro Gly His Pro Gly Ala
                 85                  90                  95

Pro Gly Val Pro Gly Gln Pro Gly Ala Arg Gly Asp Pro Gly Phe Tyr
            100                 105                 110

Gly Phe Pro Gly Met Lys Gly Lys Gly Asn Ser Gly Phe Pro Gly
        115                 120                 125

Pro Pro Gly Pro Pro Gly Gln Ser Gly Pro Lys Gly Pro Pro Gly Val
    130                 135                 140

Arg Gly Glu Pro Gly Thr Val Lys Ile Ile Ser Leu Pro Gly Ser Pro
145                 150                 155                 160

Gly Pro Pro Gly Ser Ala Gly Glu Pro Gly Met Gln Gly Glu Pro Gly
                165                 170                 175

Pro Pro Gly Pro Pro Gly Asp Pro Gly Pro Cys Gly Pro Lys Gly Lys
            180                 185                 190
```

```
Pro Gly Glu Asp Gly Pro Pro Gly Thr Pro Gly Pro Thr Gly Glu Lys
        195                 200                 205

Gly Asn Lys Gly Cys Lys Gly Glu Gln Gly Pro Pro Gly Ser Asp Gly
    210                 215                 220

Leu Pro Gly Leu Lys Gly Lys Pro Gly Asp Thr Gly Pro Pro Ala Ala
225                 230                 235                 240

Gly Ala Val Met Arg Gly Phe Val Phe Thr Arg His Ser Gln Thr Thr
                245                 250                 255

Ala Ile Pro Ser Cys Pro Glu Gly Thr Glu Pro Leu Tyr Ser Gly Phe
            260                 265                 270

Ser Leu Leu Phe Val Gln Gly Asn Glu Gln Ala His Gly Gln Asp Leu
        275                 280                 285

Gly Thr Leu Gly Ser Cys Leu Gln Arg Phe Thr Thr Met Pro Phe Leu
    290                 295                 300

Phe Cys Asn Ile Asn Asp Val Cys Asn Phe Ala Ser Arg Asn Asp Tyr
305                 310                 315                 320

Ser Tyr Trp Leu Ser Thr Pro Ala Met Ile Pro Met Asp Met Ala Pro
                325                 330                 335

Ile Thr Gly Arg Ala Leu Glu Pro Tyr Ile Ser Arg Cys Thr Val Cys
            340                 345                 350

Glu Gly Pro Ala Ile Ala Ile Ala Val His Ser Gln Thr Thr Asp Ile
        355                 360                 365

Pro Pro Cys Pro Ala Gly Trp Ile Ser Leu Trp Lys Gly Phe Ser Phe
    370                 375                 380

Ile Met Phe Thr Ser Ala Gly Ser Glu Gly Ala Gly Gln Ala Leu Ala
385                 390                 395                 400

Ser Pro Gly Ser Cys Leu Glu Glu Phe Arg Ala Ser Pro Phe Ile Glu
                405                 410                 415

Cys His Gly Arg Gly Thr Cys Asn Tyr Tyr Ser Asn Ser Tyr Ser Phe
            420                 425                 430

Trp Leu Ala Ser Leu Asp Pro Lys Arg Met Phe Arg Lys Pro Ile Pro
        435                 440                 445

Ser Thr Val Lys Ala Gly Glu Leu Glu Asn Ile Ile Ser Arg Cys Gln
    450                 455                 460

Val Cys Met Lys Met Arg Pro
465                 470

<210> SEQ ID NO: 3
<211> LENGTH: 657
<212> TYPE: DNA
<213> ORGANISM: Homo sapiens
<220> FEATURE:
<221> NAME/KEY: CDS
<222> LOCATION: (1)..(657)

<400> SEQUENCE: 3 caa acc aca gca att cct tca tgt cca gag ggg aca gtg cca ctc tac      48
Gln Thr Thr Ala Ile Pro Ser Cys Pro Glu Gly Thr Val Pro Leu Tyr
  1               5                  10                  15 agt ggg ttt tct ttt ctt ttt gta caa gga aat caa cga gcc cac gga      96
Ser Gly Phe Ser Phe Leu Phe Val Gln Gly Asn Gln Arg Ala His Gly
             20                  25                  30 caa gac ctt gga act ctt ggc agc tgc ctg cag cga ttt acc aca atg     144
Gln Asp Leu Gly Thr Leu Gly Ser Cys Leu Gln Arg Phe Thr Thr Met
         35                  40                  45 cca ttc tta ttc tgc aat gtc aat gat gta tgt aat ttt gca tct cga     192
Pro Phe Leu Phe Cys Asn Val Asn Asp Val Cys Asn Phe Ala Ser Arg
```

```
           50                  55                  60
aat gat tat tca tac tgg ctg tca aca cca gct ctg atg cca atg aac      240
Asn Asp Tyr Ser Tyr Trp Leu Ser Thr Pro Ala Leu Met Pro Met Asn
 65                  70                  75                  80 atg gct ccc att act ggc aga gcc ctt gag cct tat ata agc aga tgc      288
Met Ala Pro Ile Thr Gly Arg Ala Leu Glu Pro Tyr Ile Ser Arg Cys
                 85                  90                  95 act gtt tgt gaa ggt cct gcg atc gcc ata gcc gtt cac agc caa acc      336
Thr Val Cys Glu Gly Pro Ala Ile Ala Ile Ala Val His Ser Gln Thr
            100                 105                 110 act gac att cct cca tgt cct cac ggc tgg att tct ctc tgg aaa gga      384
Thr Asp Ile Pro Pro Cys Pro His Gly Trp Ile Ser Leu Trp Lys Gly
        115                 120                 125 ttt tca ttc atc atg ttc aca agt gca ggt tct gag ggc gcc ggg caa      432
Phe Ser Phe Ile Met Phe Thr Ser Ala Gly Ser Glu Gly Ala Gly Gln
    130                 135                 140 gca ctg gcc tcc ccc ggc tcc tgc ctg gaa gaa ttc cga gcc agc cca      480
Ala Leu Ala Ser Pro Gly Ser Cys Leu Glu Glu Phe Arg Ala Ser Pro
145                 150                 155                 160 ttt cta gaa tgt cat gga aga gga acg tgc aac tac tat tca aat tcc      528
Phe Leu Glu Cys His Gly Arg Gly Thr Cys Asn Tyr Tyr Ser Asn Ser
                165                 170                 175 tac agt ttc tgg ctg gct tca tta aac cca gaa aga atg ttc aga aag      576
Tyr Ser Phe Trp Leu Ala Ser Leu Asn Pro Glu Arg Met Phe Arg Lys
            180                 185                 190 cct att cca tca act gtg aaa gct ggg gaa tta gaa aaa ata ata agt      624
Pro Ile Pro Ser Thr Val Lys Ala Gly Glu Leu Glu Lys Ile Ile Ser
        195                 200                 205 cgc tgt cag gtg tgc atg aag aaa aga cac tga                          657
Arg Cys Gln Val Cys Met Lys Lys Arg His
    210                 215

<210> SEQ ID NO: 4
<211> LENGTH: 218
<212> TYPE: PRT
<213> ORGANISM: Homo sapiens

<400> SEQUENCE: 4

Gln Thr Thr Ala Ile Pro Ser Cys Pro Glu Gly Thr Val Pro Leu Tyr
 1               5                  10                  15

Ser Gly Phe Ser Phe Leu Phe Val Gln Gly Asn Gln Arg Ala His Gly
            20                  25                  30

Gln Asp Leu Gly Thr Leu Gly Ser Cys Leu Gln Arg Phe Thr Thr Met
        35                  40                  45

Pro Phe Leu Phe Cys Asn Val Asn Asp Val Cys Asn Phe Ala Ser Arg
    50                  55                  60

Asn Asp Tyr Ser Tyr Trp Leu Ser Thr Pro Ala Leu Met Pro Met Asn
 65                  70                  75                  80

Met Ala Pro Ile Thr Gly Arg Ala Leu Glu Pro Tyr Ile Ser Arg Cys
                 85                  90                  95

Thr Val Cys Glu Gly Pro Ala Ile Ala Ile Ala Val His Ser Gln Thr
            100                 105                 110

Thr Asp Ile Pro Pro Cys Pro His Gly Trp Ile Ser Leu Trp Lys Gly
        115                 120                 125

Phe Ser Phe Ile Met Phe Thr Ser Ala Gly Ser Glu Gly Ala Gly Gln
    130                 135                 140

Ala Leu Ala Ser Pro Gly Ser Cys Leu Glu Glu Phe Arg Ala Ser Pro
145                 150                 155                 160
```

```
Phe Leu Glu Cys His Gly Arg Gly Thr Cys Asn Tyr Tyr Ser Asn Ser
                165                 170                 175

Tyr Ser Phe Trp Leu Ala Ser Leu Asn Pro Glu Arg Met Phe Arg Lys
            180                 185                 190

Pro Ile Pro Ser Thr Val Lys Ala Gly Glu Leu Glu Lys Ile Ile Ser
        195                 200                 205

Arg Cys Gln Val Cys Met Lys Lys Arg His
    210                 215
```

```
<210> SEQ ID NO: 5
<211> LENGTH: 12
<212> TYPE: PRT
<213> ORGANISM: Homo sapiens

<400> SEQUENCE: 5

Ile Ser Arg Cys Gln Val Cys Met Lys Lys Arg His
  1               5                  10

<210> SEQ ID NO: 6
<211> LENGTH: 17
<212> TYPE: DNA
<213> ORGANISM: Artificial Sequence
<220> FEATURE:
<223> OTHER INFORMATION: Description of Artificial Sequence: PCR primer
      F1

<400> SEQUENCE: 6
aagccnggng ayacagg                                                  17

<210> SEQ ID NO: 7
<211> LENGTH: 17
<212> TYPE: DNA
<213> ORGANISM: Artificial Sequence
<220> FEATURE:
<223> OTHER INFORMATION: Description of Artificial Sequence: PCR primer
      F2

<400> SEQUENCE: 7
aagccnggng ayaccgg                                                  17

<210> SEQ ID NO: 8
<211> LENGTH: 17
<212> TYPE: DNA
<213> ORGANISM: Artificial Sequence
<220> FEATURE:
<223> OTHER INFORMATION: Description of Artificial Sequence: PCR primer
      F3

<400> SEQUENCE: 8
aagccnggng ayacggg                                                  17

<210> SEQ ID NO: 9
<211> LENGTH: 17
<212> TYPE: DNA
<213> ORGANISM: Artificial Sequence
<220> FEATURE:
<223> OTHER INFORMATION: Description of Artificial Sequence: PCR primer
      F4

<400> SEQUENCE: 9
aagccnggng ayactgg                                                  17

<210> SEQ ID NO: 10
<211> LENGTH: 20
```

<210> SEQ ID NO: 10
<211> LENGTH: 20
<212> TYPE: DNA
<213> ORGANISM: Artificial Sequence
<220> FEATURE:
<223> OTHER INFORMATION: Description of Artificial Sequence: PCR primer R1

<400> SEQUENCE: 10
tartgyctng traanacaaa                                        20

<210> SEQ ID NO: 11
<211> LENGTH: 20
<212> TYPE: DNA
<213> ORGANISM: Artificial Sequence
<220> FEATURE:
<223> OTHER INFORMATION: Description of Artificial Sequence: PCR primer R2

<400> SEQUENCE: 11
tartgyctng traanacgaa                                        20

<210> SEQ ID NO: 12
<211> LENGTH: 20
<212> TYPE: DNA
<213> ORGANISM: Artificial Sequence
<220> FEATURE:
<223> OTHER INFORMATION: Description of Artificial Sequence: PCR primer R3

<400> SEQUENCE: 12
tartgncgng traanacaaa                                        20

<210> SEQ ID NO: 13
<211> LENGTH: 20
<212> TYPE: DNA
<213> ORGANISM: Artificial Sequence
<220> FEATURE:
<223> OTHER INFORMATION: Description of Artificial Sequence: PCR primer R4

<400> SEQUENCE: 13
tartgncgng traanacgaa                                        20

<210> SEQ ID NO: 14
<211> LENGTH: 17
<212> TYPE: DNA
<213> ORGANISM: Artificial Sequence
<220> FEATURE:
<223> OTHER INFORMATION: Description of Artificial Sequence: PCR primer FA

<400> SEQUENCE: 14
gcnggncgng tnatgcg                                           17

<210> SEQ ID NO: 15
<211> LENGTH: 17
<212> TYPE: DNA
<213> ORGANISM: Artificial Sequence
<220> FEATURE:
<223> OTHER INFORMATION: Description of Artificial Sequence: PCR primer FB

<400> SEQUENCE: 15
gcnggncgng tnatgag                                           17

<210> SEQ ID NO: 16
<211> LENGTH: 19
<212> TYPE: DNA

-continued

```
<213> ORGANISM: Artificial Sequence
<220> FEATURE:
<223> OTHER INFORMATION: Description of Artificial Sequence: PCR primer
      FC

<400> SEQUENCE: 16
gtnttyacna grcaytatc                                                    19

<210> SEQ ID NO: 17
<211> LENGTH: 22
<212> TYPE: DNA
<213> ORGANISM: Artificial Sequence
<220> FEATURE:
<223> OTHER INFORMATION: Description of Artificial Sequence: PCR primer
      FD

<400> SEQUENCE: 17
ccaggmgaya chggncchcc ag                                                22

<210> SEQ ID NO: 18
<211> LENGTH: 21
<212> TYPE: DNA
<213> ORGANISM: Artificial Sequence
<220> FEATURE:
<223> OTHER INFORMATION: Description of Artificial Sequence: PCR primer
      RA

<400> SEQUENCE: 18
caggaagggc atkgtgctga a                                                 21

<210> SEQ ID NO: 19
<211> LENGTH: 20
<212> TYPE: DNA
<213> ORGANISM: Artificial Sequence
<220> FEATURE:
<223> OTHER INFORMATION: Description of Artificial Sequence: PCR primer
      RB

<400> SEQUENCE: 19
ggsgcctcac acacagmaca                                                   20

<210> SEQ ID NO: 20
<211> LENGTH: 20
<212> TYPE: DNA
<213> ORGANISM: Artificial Sequence
<220> FEATURE:
<223> OTHER INFORMATION: Description of Artificial Sequence: PCR primer
      RC

<400> SEQUENCE: 20
ttgcagwaca ggaagggcat                                                   20

<210> SEQ ID NO: 21
<211> LENGTH: 17
<212> TYPE: DNA
<213> ORGANISM: Artificial Sequence
<220> FEATURE:
<223> OTHER INFORMATION: Description of Artificial Sequence: PCR primer
      RD

<400> SEQUENCE: 21
ttgcagwaca ggaaggg                                                      17

<210> SEQ ID NO: 22
<211> LENGTH: 23
<212> TYPE: DNA
<213> ORGANISM: Artificial Sequence
```

```
<220> FEATURE:
<223> OTHER INFORMATION: Description of Artificial Sequence: PCR primer
     F9*

<400> SEQUENCE: 22
cccgatgggt tgccaggatc cat                                              23

<210> SEQ ID NO: 23
<211> LENGTH: 20
<212> TYPE: DNA
<213> ORGANISM: Artificial Sequence
<220> FEATURE:
<223> OTHER INFORMATION: Description of Artificial Sequence: PCR primer
     R9*

<400> SEQUENCE: 23
tgactatgcc tggtcacaag                                                  20

<210> SEQ ID NO: 24
<211> LENGTH: 6
<212> TYPE: PRT
<213> ORGANISM: Homo sapiens

<400> SEQUENCE: 24

Lys Pro Gly Asp Thr Gly
 1               5

<210> SEQ ID NO: 25
<211> LENGTH: 7
<212> TYPE: PRT
<213> ORGANISM: Homo sapiens

<400> SEQUENCE: 25

Thr His Arg Phe Ala Val Phe
 1               5

<210> SEQ ID NO: 26
<211> LENGTH: 37
<212> TYPE: DNA
<213> ORGANISM: Artificial Sequence
<220> FEATURE:
<223> OTHER INFORMATION: Description of Artificial Sequence: PCR primer
     A1

<400> SEQUENCE: 26
caagctagcg gccgctcgag atgcatctag agggccc                               37

<210> SEQ ID NO: 27
<211> LENGTH: 56
<212> TYPE: DNA
<213> ORGANISM: Artificial Sequence
<220> FEATURE:
<223> OTHER INFORMATION: Description of Artificial Sequence: PCR primer
     B1

<400> SEQUENCE: 27
gccgctagct tgtcatcgtc gtccttgtag tcggctagtg gggctgccag agccct          56

<210> SEQ ID NO: 28
<211> LENGTH: 47
<212> TYPE: DNA
<213> ORGANISM: Artificial Sequence
<220> FEATURE:
<223> OTHER INFORMATION: Description of Artificial Sequence: PCR primer
     A2

<400> SEQUENCE: 28
```

```
agctctagag tcatcgatgt taaccgcggg ccctattcta tagtgtc         47
```

<210> SEQ ID NO: 29
<211> LENGTH: 24
<212> TYPE: DNA
<213> ORGANISM: Artificial Sequence
<220> FEATURE:
<223> OTHER INFORMATION: Description of Artificial Sequence: PCR primer
      B2

<400> SEQUENCE: 29

```
ccctctagat gcatctcgag cggc                                  24
```

<210> SEQ ID NO: 30
<211> LENGTH: 26
<212> TYPE: DNA
<213> ORGANISM: Artificial Sequence
<220> FEATURE:
<223> OTHER INFORMATION: Description of Artificial Sequence: PCR primer
      A3

<400> SEQUENCE: 30

```
gctagcatct gttgatcacg gcttcc                                26
```

<210> SEQ ID NO: 31
<211> LENGTH: 29
<212> TYPE: DNA
<213> ORGANISM: Artificial Sequence
<220> FEATURE:
<223> OTHER INFORMATION: Description of Artificial Sequence: PCR primer
      B3

<400> SEQUENCE: 31

```
ccgcggtagc tgagtcaggc ttcattatg                             29
```

<210> SEQ ID NO: 32
<211> LENGTH: 53
<212> TYPE: DNA
<213> ORGANISM: Artificial Sequence
<220> FEATURE:
<223> OTHER INFORMATION: Description of Artificial Sequence: PCR primer
      A4

<400> SEQUENCE: 32

```
agtggaagac ggggacagtg ccactctaca gtgggtactc tttgctctac gtg  53
```

<210> SEQ ID NO: 33
<211> LENGTH: 66
<212> TYPE: DNA
<213> ORGANISM: Artificial Sequence
<220> FEATURE:
<223> OTHER INFORMATION: Description of Artificial Sequence: PCR primer
      B4

<400> SEQUENCE: 33

```
tgcagaagac ctgtcccctc tggacatgaa ggaattgctg ttgtttgact atgcctggtc  60
acaagg                                                            66
```

<210> SEQ ID NO: 34
<211> LENGTH: 51
<212> TYPE: DNA
<213> ORGANISM: Artificial Sequence
<220> FEATURE:
<223> OTHER INFORMATION: Description of Artificial Sequence: PCR primer
      A5

-continued

<400> SEQUENCE: 34
gagcgaagac aagaatgttc agaaagccta ttccgtccac cttgaaggca g    51

<210> SEQ ID NO: 35
<211> LENGTH: 53
<212> TYPE: DNA
<213> ORGANISM: Artificial Sequence
<220> FEATURE:
<223> OTHER INFORMATION: Description of Artificial Sequence: PCR primer
      B5

<400> SEQUENCE: 35
ggctgaagac acattctttc tgggtttaat gaggcgagcc aaaagctgta agc    53

<210> SEQ ID NO: 36
<211> LENGTH: 57
<212> TYPE: DNA
<213> ORGANISM: Artificial Sequence
<220> FEATURE:
<223> OTHER INFORMATION: Description of Artificial Sequence: PCR primer
      A6

<400> SEQUENCE: 36
cagtgaagac tcccattact ggcagagccc ttgagccatt tattagtagg tgtgctg    57

<210> SEQ ID NO: 37
<211> LENGTH: 60
<212> TYPE: DNA
<213> ORGANISM: Artificial Sequence
<220> FEATURE:
<223> OTHER INFORMATION: Description of Artificial Sequence: PCR primer
      B6

<400> SEQUENCE: 37
acgtgaagac taatgggagc catgttcatt ggcatcagct cagggtgga cagccagtac    60

<210> SEQ ID NO: 38
<211> LENGTH: 61
<212> TYPE: DNA
<213> ORGANISM: Artificial Sequence
<220> FEATURE:
<223> OTHER INFORMATION: Description of Artificial Sequence: PCR primer
      A7

<400> SEQUENCE: 38
cagcgaagac tgtcctcacg gctggatttc tctctggaaa ggctactctt ttgtgatgca    60
c    61

<210> SEQ ID NO: 39
<211> LENGTH: 55
<212> TYPE: DNA
<213> ORGANISM: Artificial Sequence
<220> FEATURE:
<223> OTHER INFORMATION: Description of Artificial Sequence: PCR primer
      B7

<400> SEQUENCE: 39
agatgaagac tgaggacatg gaggaatgtc agtggtctgg ctgtgcacgg ccatc    55

<210> SEQ ID NO: 40
<211> LENGTH: 43
<212> TYPE: DNA
<213> ORGANISM: Artificial Sequence
<220> FEATURE:
<223> OTHER INFORMATION: Description of Artificial Sequence: PCR primer
      A8

<400> SEQUENCE: 40
aatgctagca acctggacaa cgagaggctt ccttgtgacc agg    43

<210> SEQ ID NO: 41
<211> LENGTH: 29
<212> TYPE: DNA
<213> ORGANISM: Artificial Sequence
<220> FEATURE:
<223> OTHER INFORMATION: Description of Artificial Sequence: PCR primer
      B8

<400> SEQUENCE: 41
gacatcgatc tgagtcaggc ttcattatg    29

<210> SEQ ID NO: 42
<211> LENGTH: 58
<212> TYPE: DNA
<213> ORGANISM: Artificial Sequence
<220> FEATURE:
<223> OTHER INFORMATION: Description of Artificial Sequence: PCR primer
      A9

<400> SEQUENCE: 42
acgtgaagac tcaggtgtgc atgaagaaaa gacactaatg aagcctgact cagctagg    58

<210> SEQ ID NO: 43
<211> LENGTH: 57
<212> TYPE: DNA
<213> ORGANISM: Artificial Sequence
<220> FEATURE:
<223> OTHER INFORMATION: Description of Artificial Sequence: PCR primer
      B9

<400> SEQUENCE: 43
cttcgaagac acacctgaca gcgacttatt attttttcca gctcccctgc cttcaag    57

<210> SEQ ID NO: 44
<211> LENGTH: 65
<212> TYPE: DNA
<213> ORGANISM: Artificial Sequence
<220> FEATURE:
<223> OTHER INFORMATION: Description of Artificial Sequence: PCR primer
      A10

<400> SEQUENCE: 44
atatgctagc tggtttgaaa ggaaaacgtg gagacagtgg atcacctgca acctggacaa    60
cgaga    65

<210> SEQ ID NO: 45
<211> LENGTH: 29
<212> TYPE: DNA
<213> ORGANISM: Artificial Sequence
<220> FEATURE:
<223> OTHER INFORMATION: Description of Artificial Sequence: PCR primer
      B10

<400> SEQUENCE: 45
gacatcgatc tgagtcaggc ttcattatg    29

<210> SEQ ID NO: 46
<211> LENGTH: 47
<212> TYPE: DNA
<213> ORGANISM: Artificial Sequence
<220> FEATURE:
<223> OTHER INFORMATION: Description of Artificial Sequence: PCR primer

```
        A11

<400> SEQUENCE: 46
atatgctagc agggcctcca ggcaccccat ctgttgatca cggcttc              47

<210> SEQ ID NO: 47
<211> LENGTH: 29
<212> TYPE: DNA
<213> ORGANISM: Artificial Sequence
<220> FEATURE:
<223> OTHER INFORMATION: Description of Artificial Sequence: PCR primer
      B11

<400> SEQUENCE: 47
gacatcgatc tgagtcaggc ttcattatg                                  29

<210> SEQ ID NO: 48
<211> LENGTH: 35
<212> TYPE: DNA
<213> ORGANISM: Artificial Sequence
<220> FEATURE:
<223> OTHER INFORMATION: Description of Artificial Sequence: PCR primer
      A12

<400> SEQUENCE: 48
gatcgaagac caccgtgaag gcagggagc tggaa                            35

<210> SEQ ID NO: 49
<211> LENGTH: 34
<212> TYPE: DNA
<213> ORGANISM: Artificial Sequence
<220> FEATURE:
<223> OTHER INFORMATION: Description of Artificial Sequence: PCR primer
      B12

<400> SEQUENCE: 49
cagtgaagac tcacggtgga cggaataggc tttc                            34

<210> SEQ ID NO: 50
<211> LENGTH: 4
<212> TYPE: PRT
<213> ORGANISM: Artificial Sequence
<220> FEATURE:
<223> OTHER INFORMATION: Description of Artificial Sequence: Chimeric
      construct C1 alpha1

<400> SEQUENCE: 50

Ser Val Asp His
  1

<210> SEQ ID NO: 51
<211> LENGTH: 6
<212> TYPE: PRT
<213> ORGANISM: Artificial Sequence
<220> FEATURE:
<223> OTHER INFORMATION: Description of Artificial Sequence: Chimeric
      construct C1 alpha3

<400> SEQUENCE: 51

Ala Thr Trp Thr Thr Arg
  1               5

<210> SEQ ID NO: 52
<211> LENGTH: 15
<212> TYPE: PRT
<213> ORGANISM: Artificial Sequence
<220> FEATURE:
```

```
<223> OTHER INFORMATION: Description of Artificial Sequence: Chimeric
      construct C2 alpha1

<400> SEQUENCE: 52

Ile Asp Asp Pro Gln Cys Pro Ser Gly Thr Lys Ile Leu Tyr His
  1               5                  10                  15

<210> SEQ ID NO: 53
<211> LENGTH: 15
<212> TYPE: PRT
<213> ORGANISM: Artificial Sequence
<220> FEATURE:
<223> OTHER INFORMATION: Description of Artificial Sequence: Chimeric
      construct C2 alpha3

<400> SEQUENCE: 53

Thr Ala Ile Pro Ser Cys Pro Glu Gly Thr Val Pro Leu Tyr Ser
  1               5                  10                  15

<210> SEQ ID NO: 54
<211> LENGTH: 12
<212> TYPE: PRT
<213> ORGANISM: Artificial Sequence
<220> FEATURE:
<223> OTHER INFORMATION: Description of Artificial Sequence: Chimeric
      construct C3 alpha1

<400> SEQUENCE: 54

Thr Ile Glu Arg Ser Glu Met Phe Lys Lys Pro Thr
  1               5                  10

<210> SEQ ID NO: 55
<211> LENGTH: 12
<212> TYPE: PRT
<213> ORGANISM: Artificial Sequence
<220> FEATURE:
<223> OTHER INFORMATION: Description of Artificial Sequence: Chimeric
      construct C3 alpha3

<400> SEQUENCE: 55

Ser Leu Asn Pro Glu Arg Met Phe Arg Lys Pro Ile
  1               5                  10

<210> SEQ ID NO: 56
<211> LENGTH: 14
<212> TYPE: PRT
<213> ORGANISM: Artificial Sequence
<220> FEATURE:
<223> OTHER INFORMATION: Description of Artificial Sequence: Chimeric
      construct C4 alpha1

<400> SEQUENCE: 56

Arg Thr His Val Ser Arg Cys Gln Val Cys Met Arg Arg Thr
  1               5                  10

<210> SEQ ID NO: 57
<211> LENGTH: 15
<212> TYPE: PRT
<213> ORGANISM: Artificial Sequence
<220> FEATURE:
<223> OTHER INFORMATION: Description of Artificial Sequence: Chimeric
      construct C4 alpha3

<400> SEQUENCE: 57

Glu Lys Ile Ile Ser Arg Cys Gln Val Cys Met Lys Lys Arg His
  1               5                  10                  15
```

```
<210> SEQ ID NO: 58
<211> LENGTH: 15
<212> TYPE: PRT
<213> ORGANISM: Artificial Sequence
<220> FEATURE:
<223> OTHER INFORMATION: Description of Artificial Sequence: Chimeric
      construct C5 alpha1

<400> SEQUENCE: 58

Pro Met Pro Met Ser Met Ala Pro Ile Thr Gly Glu Asn Ile Arg
 1               5                  10                  15

<210> SEQ ID NO: 59
<211> LENGTH: 15
<212> TYPE: PRT
<213> ORGANISM: Artificial Sequence
<220> FEATURE:
<223> OTHER INFORMATION: Description of Artificial Sequence: Chimeric
      construct C5 alpha3

<400> SEQUENCE: 59

Leu Met Pro Met Asn Met Ala Pro Ile Thr Gly Arg Ala Leu Glu
 1               5                  10                  15

<210> SEQ ID NO: 60
<211> LENGTH: 15
<212> TYPE: PRT
<213> ORGANISM: Artificial Sequence
<220> FEATURE:
<223> OTHER INFORMATION: Description of Artificial Sequence: Chimeric
      construct C6 alpha1

<400> SEQUENCE: 60

Ile Gln Ile Pro Pro Cys Pro Ser Gly Trp Ser Ser Leu Trp Ile
 1               5                  10                  15

<210> SEQ ID NO: 61
<211> LENGTH: 15
<212> TYPE: PRT
<213> ORGANISM: Artificial Sequence
<220> FEATURE:
<223> OTHER INFORMATION: Description of Artificial Sequence: Chimeric
      construct C6 alpha3

<400> SEQUENCE: 61

Thr Asp Ile Pro Pro Cys Pro His Gly Trp Ile Ser Leu Trp Lys
 1               5                  10                  15

<210> SEQ ID NO: 62
<211> LENGTH: 24
<212> TYPE: PRT
<213> ORGANISM: Artificial Sequence
<220> FEATURE:
<223> OTHER INFORMATION: Description of Artificial Sequence: Chimeric
      construct C7 alpha1

<400> SEQUENCE: 62

Gly Leu Pro Gly Ser Met Gly Pro Pro Gly Thr Pro Ser Val Asp His
 1               5                  10                  15

Gly Phe Leu Val Thr Arg His Ser
            20

<210> SEQ ID NO: 63
<211> LENGTH: 26
<212> TYPE: PRT
<213> ORGANISM: Artificial Sequence
<220> FEATURE:
<223> OTHER INFORMATION: Description of Artificial Sequence: Chimeric
```

-continued

```
               construct C7 alpha3

<400> SEQUENCE: 63

Gly Leu Lys Gly Lys Arg Gly Asp Ser Gly Ser Pro Ala Thr Trp Thr
 1               5                   10                  15

Thr Arg Gly Phe Val Phe Thr Arg His Ser
            20                  25

<210> SEQ ID NO: 64
<211> LENGTH: 35
<212> TYPE: PRT
<213> ORGANISM: Artificial Sequence
<220> FEATURE:
<223> OTHER INFORMATION: Description of Artificial Sequence: Chimeric
      construct C8 alpha1

<400> SEQUENCE: 64

Thr Ile Glu Arg Ser Glu Met Phe Lys Lys Pro Thr Pro Ser Thr Leu
 1               5                   10                  15

Lys Ala Gly Glu Leu Arg Thr His Val Ser Arg Cys Gln Val Cys Met
            20                  25                  30

Arg Arg Thr
        35

<210> SEQ ID NO: 65
<211> LENGTH: 36
<212> TYPE: PRT
<213> ORGANISM: Artificial Sequence
<220> FEATURE:
<223> OTHER INFORMATION: Description of Artificial Sequence: Chimeric
      construct C8 alpha3

<400> SEQUENCE: 65

Ser Leu Asn Pro Glu Arg Met Phe Arg Lys Pro Ile Pro Ser Thr Val
 1               5                   10                  15

Lys Ala Gly Glu Leu Glu Lys Ile Ile Ser Arg Cys Gln Val Cys Met
            20                  25                  30

Lys Lys Arg His
        35
```